US007790468B2

(12) United States Patent  
Yoshimura et al.

(10) Patent No.: US 7,790,468 B2  
(45) Date of Patent: Sep. 7, 2010

(54) TEST OBJECT RECEPTACLE, TEST APPARATUS, AND TEST METHOD

(75) Inventors: Chisato Yoshimura, Nagoya (JP); Hideo Nakano, Iwakura (JP); Takanori Ishishika, Nagoya (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 1141 days.

(21) Appl. No.: 11/071,369

(22) Filed: Mar. 4, 2005

(65) Prior Publication Data  
US 2005/0202733 A1    Sep. 15, 2005

(30) Foreign Application Priority Data  
Mar. 9, 2004    (JP)    .............. 2004-066206

(51) Int. Cl.  
*G01N 21/07* (2006.01)  
*G01N 21/03* (2006.01)  
*B04B 1/00* (2006.01)

(52) U.S. Cl. .................... 436/165; 422/64; 422/72; 422/101; 422/102; 436/45; 494/43; 494/67; 494/68; 494/75

(58) Field of Classification Search .......... 422/64, 422/72, 101–102; 436/45; 494/43, 67–78, 494/75  
See application file for complete search history.

(56) References Cited

U.S. PATENT DOCUMENTS

| | | | | | |
|---|---|---|---|---|---|
| 957,092 | A | * | 5/1910 | Ramstrom | 494/73 |
| 1,006,622 | A | * | 10/1911 | Bailey | 494/75 |
| 1,936,524 | A | * | 11/1933 | Placek | 261/86 |
| 3,586,484 | A | * | 6/1971 | Anderson | 436/45 |
| 3,698,626 | A | * | 10/1972 | Kotrappa et al. | 494/26 |
| 3,759,666 | A | * | 9/1973 | Hill, Jr. | 435/14 |
| 3,873,217 | A | * | 3/1975 | Anderson et al. | 356/246 |
| 4,225,558 | A | * | 9/1980 | Peterson et al. | 422/72 |
| 4,237,234 | A | * | 12/1980 | Meunier | 435/287.7 |
| 4,262,841 | A | * | 4/1981 | Berber et al. | 494/66 |
| 4,279,862 | A | * | 7/1981 | Bretaudiere et al. | 422/72 |

(Continued)

FOREIGN PATENT DOCUMENTS

EP    0 417 305 A1    3/1991

(Continued)

OTHER PUBLICATIONS

Ito, Y. et al, Journal of Chromatography, A 2003, 1017, 71-81.*

*Primary Examiner*—Arlen Soderquist  
(74) *Attorney, Agent, or Firm*—Oliff & Berridge, PLC

(57) ABSTRACT

A test object receptacle, capable of measuring a test object in a wide range of concentrations with good accuracy and within a short time, contains a plurality of fine protruding portions inside grooves. The test object receptacle can fix antigens, antibodies and test objects faster than without the protruding portions. Furthermore, the protruding portions are so formed that the surface area thereof increases gradually to the downstream with respect to the movement direction of the test object in the grooves, the detection intensity (intensity of color development) of the test object is not saturated downstream of the grooves even when the test object has a high concentration. For this reason, the test object can be detected within a short time and the measurements can be conducted within a wide concentration range.

44 Claims, 17 Drawing Sheets

U.S. PATENT DOCUMENTS

| | | | | |
|---|---|---|---|---|
| 4,373,812 | A * | 2/1983 | Stein et al. | 356/246 |
| 4,387,992 | A * | 6/1983 | Swartz | 356/246 |
| 4,456,581 | A * | 6/1984 | Edelmann et al. | 422/72 |
| 4,479,790 | A * | 10/1984 | Bocckino et al. | 494/85 |
| 4,509,856 | A * | 4/1985 | Lee | 356/246 |
| 4,814,144 | A * | 3/1989 | Edelmann et al. | 422/102 |
| 4,938,927 | A * | 7/1990 | Kelton et al. | 422/64 |
| 5,186,896 | A * | 2/1993 | Bouchee et al. | 422/72 |
| 5,225,163 | A * | 7/1993 | Andrews | 422/61 |
| 5,238,652 | A * | 8/1993 | Sun et al. | 422/61 |
| 5,256,376 | A * | 10/1993 | Callan et al. | 422/102 |
| 5,304,487 | A * | 4/1994 | Wilding et al. | 435/29 |
| 5,631,166 | A * | 5/1997 | Jewell | 436/45 |
| 5,707,799 | A | 1/1998 | Hansmann et al. | |
| 5,855,848 | A * | 1/1999 | Zuccato | 422/72 |
| 5,869,347 | A * | 2/1999 | Josef et al. | 436/536 |
| 5,952,173 | A | 9/1999 | Hansmann et al. | |
| 5,994,696 | A * | 11/1999 | Tai et al. | 250/288 |
| 6,013,513 | A * | 1/2000 | Reber et al. | 435/288.5 |
| 6,030,581 | A * | 2/2000 | Virtanen | 422/68.1 |
| 6,156,273 | A | 12/2000 | Regnier et al. | 422/70 |
| 6,312,901 | B2 * | 11/2001 | Virtanen | 435/6 |
| 6,319,469 | B1 * | 11/2001 | Mian et al. | 422/64 |
| 6,368,871 | B1 | 4/2002 | Christel et al. | 436/180 |
| 6,399,394 | B1 | 6/2002 | Dahm et al. | 436/180 |
| 6,454,924 | B2 * | 9/2002 | Jedrzejewski et al. | 204/601 |
| 6,506,344 | B1 * | 1/2003 | Fickenscher et al. | 422/72 |
| 6,527,432 | B2 * | 3/2003 | Kellogg et al. | 366/182.1 |
| 6,582,662 | B1 * | 6/2003 | Kellogg et al. | 422/72 |
| 6,632,656 | B1 * | 10/2003 | Thomas et al. | 435/288.5 |
| 6,884,395 | B2 * | 4/2005 | Tooke et al. | 422/64 |
| 6,932,951 | B1 * | 8/2005 | Losey et al. | 422/211 |
| 7,026,131 | B2 * | 4/2006 | Hurt et al. | 435/7.25 |
| 7,078,203 | B1 * | 7/2006 | Xiong et al. | 435/183 |
| 7,192,560 | B2 * | 3/2007 | Parthasarathy et al. | 422/101 |
| 7,201,873 | B2 | 4/2007 | Tanaka et al. | |
| 7,251,210 | B2 * | 7/2007 | Coombs et al. | 369/275.4 |
| 7,387,898 | B1 | 6/2008 | Gordon | 436/165 |
| 2001/0019842 | A1 * | 9/2001 | Kitamura et al. | 436/45 |
| 2003/0049563 | A1 | 3/2003 | Iida et al. | |
| 2003/0129665 | A1 * | 7/2003 | Selvan et al. | 435/7.2 |
| 2003/0143114 | A1 * | 7/2003 | Andersson et al. | 422/64 |
| 2003/0211010 | A1 * | 11/2003 | Nagaoka et al. | 422/64 |

FOREIGN PATENT DOCUMENTS

| | | |
|---|---|---|
| EP | 0 430 248 A2 | 6/1991 |
| EP | 0 504 432 A1 | 9/1992 |
| JP | A 3-223674 | 10/1991 |
| JP | A 3-225278 | 10/1991 |
| JP | A 5-5471 | 1/1993 |
| JP | A 5-5741 | 1/1993 |
| JP | A 10-506991 | 7/1998 |
| JP | A-2003-130883 | 5/2003 |
| JP | A-2003-307521 | 10/2003 |
| JP | A 2004-45357 | 2/2004 |

* cited by examiner

FIG. 7A ENLARGED VIEW
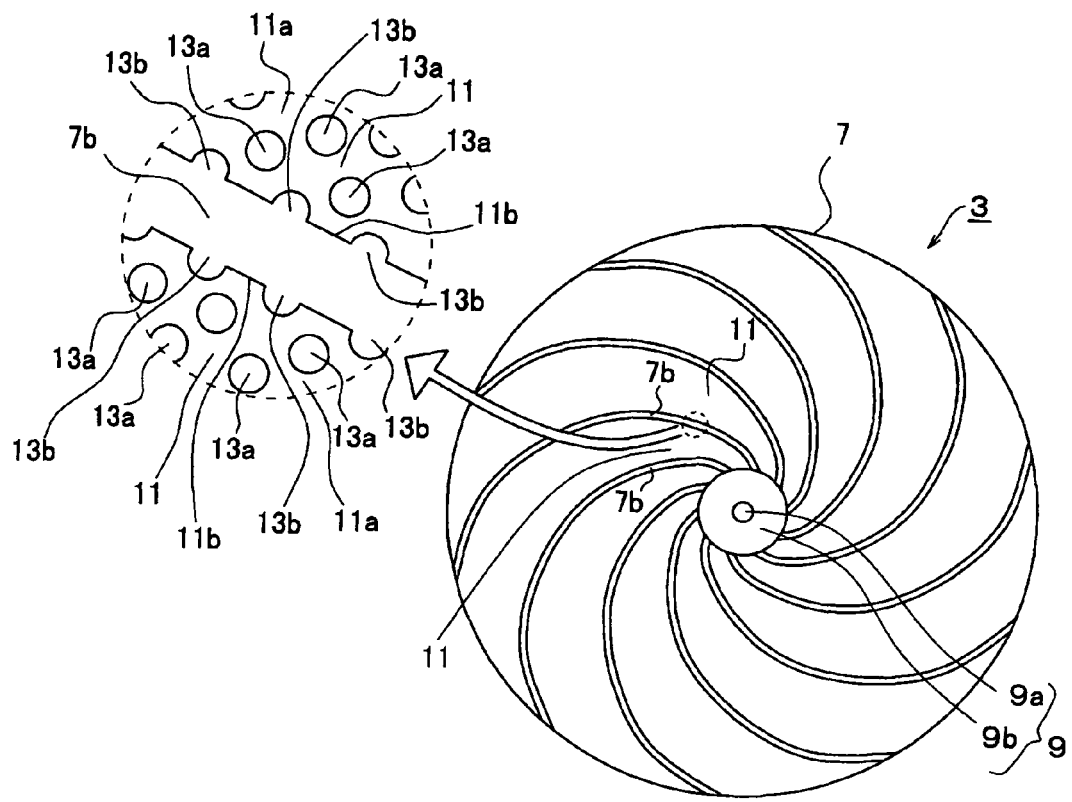
FIG.7B
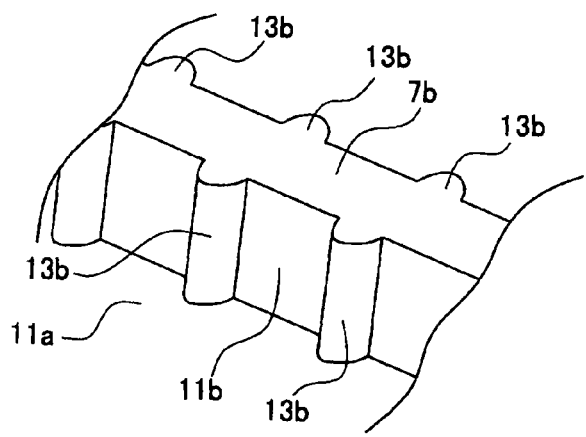

TEST OBJECT RECEPTACLE, TEST APPARATUS, AND TEST METHOD

BACKGROUND OF THE INVENTION

1. Field of the Invention

The present invention relates to a test object receptacle, a test apparatus, and a test method for conducting tests using intermolecular interaction such as antigen-antibody reactions.

2. Description of the Related Art

Enzyme-linked immunosorbent assay (ELISA) has been used in recent years mainly in the field of medicine or biotechnology for quantitatively determining antigens or antibodies. With this method the antigen-antibody reaction between an antibody or antigen and a measurement substance is traced with the enzyme activity as an indicator and the antigen or antibody is assayed based on the results obtained. Some of the ELISA methods use bioluminescence, chemiluminescence, or fluorescence. Such an assay is conducted by causing a reaction of an enzyme-labeled antigen or antibody and a substrate, detecting the luminescence or fluorescence produced in this enzyme reaction with a photodetector, and measuring the intensity thereof.

In immunoassay using a microplate as a reactor for immunoassay, first, an antigen corresponding to an antibody to be measured or an antibody corresponding to an antigen to be measured, is converted into a solid phase on the well bottom. Then, a sample containing the antibody or antigen, which is to be measured, is added, and an antigen-antibody reaction is induced. A labeled antigen or labeled antibody is then added and the non-adsorbed labeled antigen or labeled antibody is washed. A substrate liquid is then added, an enzyme substrate reaction is induced, and the enzyme activity generated in this process is measured by absorption photometry, fluorophotometry or the like to determine quantitatively the antigen or antibody.

Japanese Patent Application Laid-open No. H5-5741 described the use of a centrifugal force in immunoassay. Furthermore, a method using a simple kit based on immunochromatography is known as another immunoassay method.

SUMMARY OF THE INVENTION

However, the problems associated with the conventional ELISA method were, for example, that a large apparatus was required, several hours were needed for the test, and know-how was required for the test. Furthermore, with the simple kit used in the immunochromatography, the problem was that the quantitative determination ability was poor, sensitivity was low, and measurement results were greatly affected by the purity of sample liquid.

With the foregoing in view, it is an object of the present invention to provide a compact test object receptacle, a test apparatus and a test method making it possible to conduct measurements in an easy manner, with high sensitivity, and within a short time.

(1) The present invention provides a test object receptacle comprising a disk-like main body, which can be attached to an external rotary member, a plurality of grooves disposed radially around the central portion in the main body, and a plurality of protruding portions provided inside the grooves.

The test object receptacle in accordance with the present invention has a plurality of protruding portions inside the grooves. Because a plurality of the protruding portions have a large surface area, if a test object is supplied inside the grooves, the contact surface area of the test object and the protruding portions is increased and a large quantity of the test object can be adsorbed. Therefore, using the test object receptacle in accordance with the present invention makes it possible to test the test object with good sensitivity.

If the test object receptacle in accordance with the present invention is attached to the external rotary member and the test object receptacle is rotated in a state that the test object has been supplied to the inner peripheral side of the grooves, then a centrifugal force acts upon the test object located inside the grooves and the test object is pushed out toward the outer periphery of the grooves. The pushed test object passes between the plurality of protruding portions, while colliding therewith. In this process the test object is effectively adsorbed by the protruding portions because it passes in narrow gaps between the protruding portions. Therefore, with the present invention, the test object can be adsorbed by the test object receptacle within a short time and the test can be conducted within a short time.

The outer peripheral end of the grooves may be opened and the test object pushed by the centrifugal force may flow out. Further, liquid reservoirs may be provided in the vicinity of the outer peripheral end of the grooves and the test object may be accumulated therein.

(2) The present invention also provides a test object receptacle, which can be attached to an external rotary member, comprises a supply section for supplying the test object and moving the test object by a centrifugal force created by the rotation of the rotary member, and protruding portions provided in positions in contact with the test object in the supply section.

When the test object receptacle in accordance with the present invention can comprise protruding portions with a surface area larger than that of the flat portions in the supply section and a test object is supplied into the supply section, the contact surface area of the test object and the protruding portions is large and a large quantity of the test object can be adsorbed by the protruding portions. Therefore, if the test object receptacle in accordance with the present invention is used, the test object can be detected with good sensitivity.

Further, if the test object receptacle is attached to the external rotary member and the test object receptacle is rotated in a state that the test object has been supplied to the supply section, then a centrifugal force acts upon the test object located inside the supply section, the test object is pushed out toward the outer periphery, and moves, while colliding with the protruding portions. At this time, the test object is effectively adsorbed by the protruding portions, due to collision with the protruding portions. Therefore, in accordance with the present invention, the test object can be adsorbed in the test object receptacle within a short time and the test can be conducted within a short time.

(3) In the present invention, the supply section can be composed of a groove.

In accordance with the present invention, when the supply section is a groove and the test object is supplied into a groove, the reagent for detecting the test object may be coated only inside the groove. As a result, the quantity of the reagent used can be reduced. Moreover, because the protruding portions may be formed only inside the groove, the test object receptacle can be easily manufactured.

(4) In the present invention, the groove can be a curved groove.

In accordance with the present invention, when the groove is formed to have a curved shape, the total length of the groove is increased. Increasing the total length of the groove makes it possible to conduct the assay of the test object, for example, in the following manner. Thus, the test object can be detected in a plurality of points in the groove, the distribution of the detected quantity of the test object in each position in the groove can be computed, and the test object can be assayed by using this distribution.

(5) In the present invention, the width of a certain portion of the groove can be wider than the width of other portions.

In accordance with the present invention, for example, when a large number of protruding portions are formed in the portion of the groove with a large width and a large quantity of the test object can be adsorbed therein, the test object can be accurately detected in the portion of the groove with a large width.

(6) In the present invention, the width of the groove can increase gradually to the downstream with respect to the movement direction of the test object.

In accordance with the present invention, for example, a large number of protruding portions can be formed in the portion of the groove with a large width located on the downstream side of the groove and a large quantity of the test object can be adsorbed therein. Therefore, even when the quantity of the test object is large, the detection is possible without diluting the test object.

(7) In the present invention, changes in the width of the groove can be continuous.

In accordance with the present invention, when changes in the width of the groove are continuous, the test object smoothly flows inside the groove and is uniformly adsorbed by the protruding portions.

(8) In the present invention, at least some of the protruding portions can be formed integrally with the side surface of the groove.

In accordance with the present invention, when at least some of the protruding portions are formed integrally with the side surface of the groove, the test object can be adsorbed in a larger amount and with better efficiency than in the case where the protruding portions are provided separately from the side surface of the grooves.

Further, in accordance with the present invention, there can be protruding portions formed integrally with the side surface of the groove. Therefore, by contrast with the case where no protruding portions are provided in the vicinity of both ends of the groove (portions close to the side surface), the test object is prevented from preferentially flowing in the vicinity of both ends of the groove and insufficient adsorption by the protruding portions is avoided.

(9) In the present invention, the groove can be a branched groove.

When the groove in accordance with the present invention, for example, is a groove which is branched into two or more grooves on the upstream side, it again becomes a single groove on the downstream side after the two grooves merge together in a certain place (branching point). In this case, for example, the test object can be supplied to one of the two or more grooves located on the upstream side and a reagent can be supplied to the other groove. As a result, the test object and the reagent merge together in the branching point and the test object can be detected in the groove located downstream of the branching point.

Further, the groove in accordance with the present invention, for example, may be a groove which is a single groove on the upstream side, but is branched into two or more in a branching point and assumes a form of two or more grooves on the downstream side. In this case, for example, the test object supplied into a single groove located on the upstream side is divided into two or more branched on the downstream, thereby making it possible to conduct the test in each groove.

(10) In the present invention, the branching point at which the groove is branched can be on the rotation center side of the rotary member.

When the groove in accordance with the present invention is branched on the rotation center side of the rotary member (on the side closer to the rotation center that the central point in the longitudinal direction of the groove), a reagent can be introduced at the initial stage of the reaction. In other words, if there are two or more grooves on the upstream side of the branching point, the detection object is supplied into one of them, and the reagent is supplied into the other groove, then the branching point, as described hereinabove, is located on the side of the rotation center (that is, on the upstream side). Therefore, the test object and reagent are mixed and reaction is induced at the initial stage. As a result, the detection can be accurately conducted even if the reagent changes easily.

(11) In the present invention, the test object receptacle can have a plurality of the grooves.

When the test object receptacle in accordance with the present invention has a plurality of grooves and, for example, different test objects are supplied to a plurality of grooves, all the test objects can be detected at the same time.

(12) In the present invention, a plurality of grooves can be formed radially.

In the test object receptacle in accordance with the present invention, when a plurality of the grooves are formed radially and the rotation center of the rotary member is made to serve as a center of radial grooves, then a centrifugal force will be uniformly applied to the test objects in each groove. As a result, the detection of the test object can be conducted under identical conditions in each groove.

(13) In the present invention, the rotation center for the rotation provided by the rotary member can be the center of a plurality of grooves formed radially.

In the test object receptacle in accordance with the present invention, when a plurality of grooves are formed radially and the rotation center of the rotary member is located in the center of radial grooves, a centrifugal force will be uniformly applied to the test objects in each groove. As a result, the detection of the test object can be conducted under identical conditions in each groove.

(14) In the present invention, at least some of the grooves can have a radial portion extending in the radial direction (direction that becomes the radial direction during rotation of the rotary member when the test object receptacle is attached to the rotary member) of the rotary member and a circumferential portion extending in the circumferential direction (direction that becomes the circumferential direction during rotation of the rotary member when the test object receptacle is attached to the rotary member) of the rotary member on the downstream side of the radial portion.

When the grooves in accordance with the present invention have a radial portion and a circumferential portion, the total length thereof is large. As a result, the adsorbed quantity of the test object can be increased and the test object can be detected with high sensitivity.

(15) In the present invention, at least some of the grooves can have a second radial portion extending in the rotation direction of the rotary member on the downstream side of the circumferential portion, in addition to the radial portion and circumferential portion.

When the grooves in accordance with the present invention have a second radial portion in addition to the radial portion and the circumferential portion, the total length thereof is large. As a result, the adsorbed quantity of the test object can be increased and the test object can be detected with high sensitivity.

(16) In the present invention, the surface area of the protruding portions contained in a unit length of the groove in at least some of the grooves can increase gradually to the downstream with respect to the movement direction of the test object.

In accordance with the present invention, when the surface area of the protruding portions contained in a unit length of the grooves increases gradually to the downstream with respect to the movement direction of the test object, a large quantity of the test object can be adsorbed by the protruding portions on the downstream side. As a result, measurements can be conducted even when the test object has a high concentration.

(17) In the present invention, the number of the protruding portions contained in a unit length of the groove in at least some of the grooves can increase gradually to the downstream with respect to the movement direction of the test object.

In accordance with the present invention, when the number of the protruding portions contained in a unit length of the grooves increases gradually to the downstream, the surface area of the protruding portions contained in a unit length of the grooves also increases gradually to the downstream. As a result, a large quantity of the test object can be adsorbed by the protruding portions on the downstream side of the grooves and measurements can be conducted even when the test object has a high concentration.

(18) In the present invention, in at least some of the grooves, the protruding portions can protrude perpendicularly to the surface where the grooves are formed.

In the test object receptacle in accordance with the present invention, when the protruding portions protrude perpendicularly to the surface where the grooves are formed, the manufacturing process using a mold can be employed and the productivity is good.

(19) In the present invention, the depth of the supply section can be constant.

In accordance with the present invention, when the depth of the supply section is constant, the depth of the test object present in the supply section is also constant. Therefore, when the detection object is detected by using a transmission light, the test object can be detected in a simple manner without conducting correction with respect to the depth.

(20) In the present invention, a supply section can become deeper gradually to the downstream with respect to the movement direction of the test object.

In accordance with the present invention, when the depth of the supply section increases gradually to the downstream of the supply section, for example, high protruding portions can be provided downstream of the supply section and the surface area of the protruding portions can be increased. As a result, even when the test object has a high concentration, the detection is possible without diluting the test object.

(21) In the present invention, changes in the depth of the supply section can be continuous.

In accordance with the present invention, when changes in the depth of the supply section are continuous, the test object smoothly flows inside the supply section and is uniformly adsorbed by the protruding portions.

(22) In the present invention, in at least some of the supply sections, the height of the protruding portions can be directly proportional to the depth of the supply section in the location of the protruding portions.

In accordance with the present invention, when the height of the protruding portions is directly proportional to the depth of the supply section in the location of the protruding portions, for example, the height of the protruding portions can reach the upper side of the supply section correspondingly to the depth of the supply section. As a result, the test object is prevented from moving over the top of the protruding portions. Therefore, the test object can be adsorbed by the protruding portions with good efficiency. Employing the present invention makes it possible to detect the test object accurately.

Further, the protruding portions can be prevented from protruding from the supply section correspondingly to the depth of the supply section. Therefore, the supply section can be covered with a lid. As a result, the test object can be prevented from leaking from the supply section.

(23) In the present invention, in at least some of the supply sections, the surface area of the protruding portions provided in the supply sections can be constant.

In accordance with the present invention, when the surface area of the protruding portions is constant, the adsorption quantity of the test object adsorbed per one protruding portion is constant. As a result, the adsorption quantity of the test object can be computed based on the number of protruding portions and the test object can be assayed.

(24) In the present invention, in at least some of the supply sections, the shape of the protruding portions provided in the supply sections can be constant.

In accordance with the present invention, when the shape of the protruding portions is constant, the surface area per one protruding portion is constant and the adsorption quantity of the test object adsorbed per one protruding portion is constant. As a result, the adsorption quantity of the test object can be computed based on the number of protruding portions and the test object can be assayed.

(25) In the present invention, the test object receptacle can be formed to have a disk-like shape.

When the test object receptacle in accordance with the present invention has a disk-like shape, during rotation, a centrifugal force is easily applied to the test object located inside the supply section, the test object can be moved with high speed. Therefore, the test object receptacle in accordance with the present invention is used, the time required for the test is shortened.

Furthermore, because the main body has a disk-like shape, the dead space where the supply sections cannot be formed can be small and the efficiency is good. As a result, the test object receptacle in accordance with the present invention can have light weight and small size and the production cost thereof is low.

(26) In the present invention, in at least some of the supply sections, the spacing between the protruding portions can be within a range of 2 to 8 μm.

In accordance with the present invention, when the spacing between the protruding portions is 8 μm or less, the protruding portions functions as a filter and removes neutrophilic leucocytes, acidophilic leucocytes, basophilic leucocytes, and monocytes of white corpuscles which are larger than 8 μm. Furthermore, when the spacing between the protruding portions is 2 μm or more, smaller portions cannot be clogged.

(27) In the present invention, in at least some of the supply sections, the spacing between the protruding portions can be within a range of 0.3 to 2 μm.

In accordance with the present invention, when the spacing between the protruding portions is no more than 2 μm, the protruding portions function as a filter and can remove red corpuscles, white corpuscles engulfing foreign matter, blood platelets, and corpuscles which are larger than 2 μm. Furthermore, because the spacing between the protruding portions is 0.3 μm or more, smaller portions cannot be clogged.

(28) In the present invention, in at least some of the supply sections, the protruding portions provided in the supply sections can have a cylindrical shape.

In the test object receptacle in accordance with the present invention, when the protruding portions have a cylindrical shape, manufacture thereof becomes facilitated.

(29) In the present invention, in at least some of the supply sections, the protruding portions can be formed integrally with the supply sections.

In the test object receptacle in accordance with the present invention, when the protruding portions are formed integrally with the supply sections, it is not necessary to spend time on machining the protruding portions independently and the manufacturing process is facilitated.

(30) In the present invention, the test object receptacle can further comprise a reference portion for distinguishing the test object receptacle and/or distinguishing the phase in rotation of the test object receptacle.

The test object receptacle in accordance with the present invention can comprise a reference portion. Therefore, even when a plurality of test object receptacles are used, a specific test object receptacle can be easily distinguished by using the reference portion.

Further, when the test object receptacle is rotated, individual supply sections can be distinguished based on the position of the reference portion.

(31) In the present invention, the reference portion can be formed integrally with the main body of the test object receptacle.

In the test object receptacle in accordance with the present invention, when the reference portion is formed integrally with the main body of the test object receptacle, the manufacturing process is facilitated.

(32) The present invention also provides a test apparatus comprising the test object receptacle above-described, and a rotary member which is to be joined to the test object receptacle and rotated.

Using the test apparatus in accordance with the present invention makes it possible to detect a test object rapidly and with good sensitivity.

Furthermore, the size and weight of the test apparatus in accordance with the present invention can be reduced.

(33) The present invention also provides a test method of intermolecular interaction using the test object receptacle above-described, comprising the first step of supplying a test object to the supply sections, the second step of rotating the rotary member and moving the test object by a centrifugal force along the supply sections, and the third step of assaying the test object.

The test method in accordance with the present invention makes it possible to detect a test object rapidly and with good sensitivity by using the test object receptacle above-described.

(34) In the present invention, in the third step, the test object can be detected in a plurality of points in the supply sections, the distribution of the detected quantity of the test object corresponding to a position in the supply section can be computed, and the test object can be assayed by using this distribution.

With the test method in accordance with the present invention, the assay is conducted by using the distribution of the detected quantity of the test object corresponding to a position in the supply section. Therefore, the concentration of the test object can be measured in a wide range.

As a result, it is not necessary to dilute the test object and the detection can be conducted easily and rapidly.

(35) In the present invention, the test object can be assayed the surface area of the portion defined by restriction lines showing the distribution and the prescribed reference lines.

In accordance with the present invention, when the assay is conducted by using the surface of the area delineated in the above-described manner, the concentration of the test object can be measured in a wide range.

As a result, it is not necessary to dilute the test object and the detection can be conducted easily and rapidly.

(36) In the present invention, the reference lines can be a reference line relating to the distance in the radial direction of the rotary shaft of the rotary member and a reference line relating to the detected quantity.

In accordance with the present invention, selecting the above-described reference lines can make it possible to conduct accurate assay of the test object.

(37) In the present invention, in some of the reference lines, the detected quantity can be saturated, the corrected restriction line without the saturation can be computed by extrapolation and the surface area can be delineated by using the corrected restriction line.

In accordance with the present invention, even when the detected quantity is saturated in some of restriction lines, the test object can be accurately assayed.

(38) The present invention also provides a method for the manufacture of a mold for the manufacture of the test object receptacle above-described, wherein the protruding portions can be formed by lithography.

In accordance with the present invention, the mold can be manufactured by lithography. Therefore, even when the protruding portions in the test object receptacle have a fine shape, the mold accurately corresponding to this shape can be manufactured. As a result, using the method for the manufacture of the mold in accordance with the present invention makes it possible to manufacture accurately the test object receptacle above-described.

(39) In the present, X rays are used in the lithography.

In accordance with the present invention, when the mold (in particular, portions corresponding to the protruding portions) is manufactured by lithography using X rays, fine protruding portions in a high aspect ratio (a height-to-diameter ratio in cylinders constituting the protruding portions) can be formed with a high density to adsorb a larger quantity of the test object.

(40) In the present invention, the mold can be formed by machining.

In accordance with the present invention, the mold can be manufactured at low cost.

(41) In the present invention, a supply portion for supplying the test object to the supply section can have a protrusion in the center of the test object receptacle.

In accordance with the present invention, when the supply portion for supplying the test object to the supply section has a protrusion in the center of the test object receptacle, the test object supplied to the supply portion is shifted from the portion serving as the rotation center of the test object receptacle, a centrifugal force created by the rotation of the test object receptacle acts upon the test object, and the test object can be moved reliably.

(42) In the present invention, the area between the protrusion of the supply portion and the region where the protruding portions are provided can be concaved with respect to the region where the protruding portions are provided.

In accordance with the present invention, when the area between the protrusion of the supply section and the region where the protruding portions are provided is concaved with respect to the region where the protruding portions are provided, the test object supplied to the supply portion is accumulated in this concave portion and a sufficient quantity of the test object can be supplied to this supply portion, by contrast with the configuration have absolutely no recess in this portion.

(43) In the present invention, the area between the protrusion of the supply section and the region where the protruding portions are provided can be continuously sloped.

In accordance with the present invention, when the area between the protrusion of the supply section and the region where the protruding portions are provided can be continuously sloped. Therefore, when the test object supplied to the supply portion is moved by the centrifugal force, the test object can be moved smoothly, by contrast with the configuration in which a step was formed between the protrusion of the supply section and the region where the protruding portions were provided.

BRIEF DESCRIPTION OF THE DRAWINGS

FIG. 7A is a plan view showing the configuration of the test object receptacle;

FIG. 7B is a perspective view showing the structure of the grooves and protruding portions;

DESCRIPTION OF THE PREFERRED EMBODIMENTS

The preferred modes for carrying out the present invention will be described below by using working examples.

Working Example 1

Figure 1:
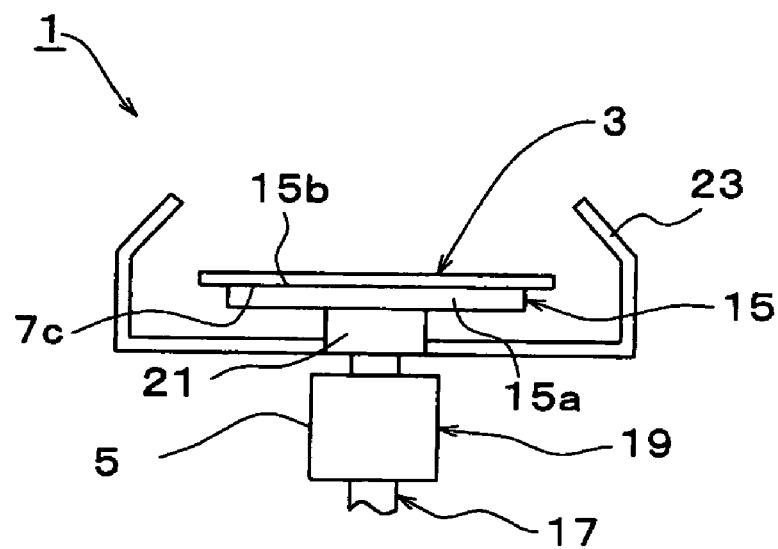
FIG. 1 is a side view showing the configuration of the rotary portion of a test apparatus.
Figure 2A:
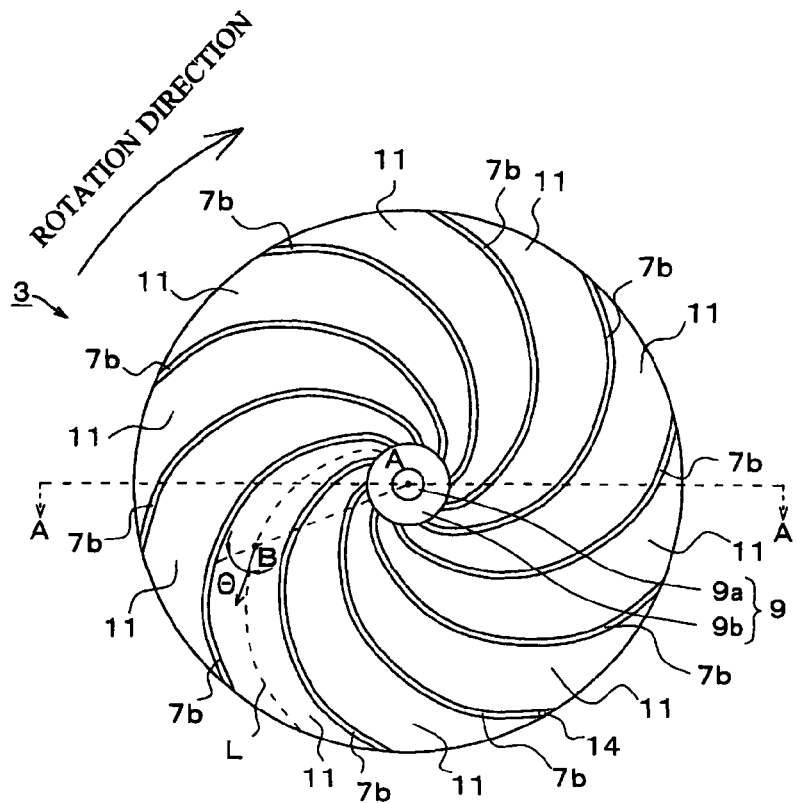
FIG. 2A is a plan view showing the configuration of the test object receptacle.
Figure 2B:
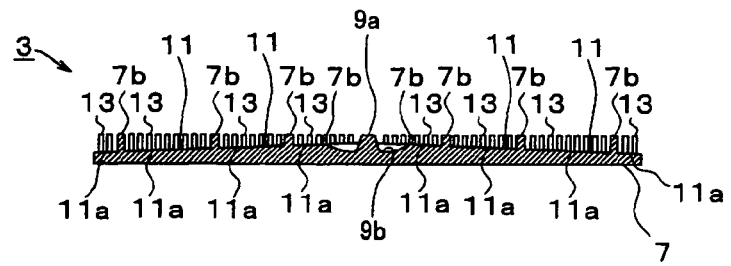
FIGS. 2B and 2C are cross-sectional views taken along the line A-A.
Figure 2C:
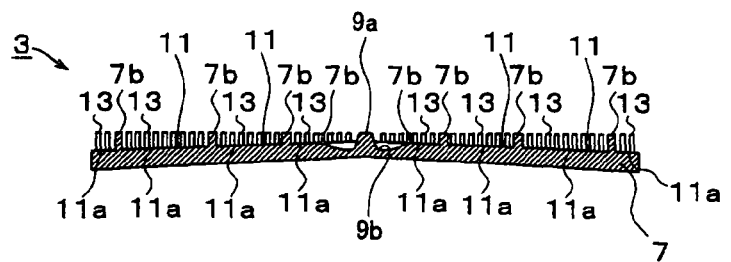
Figure 3A:
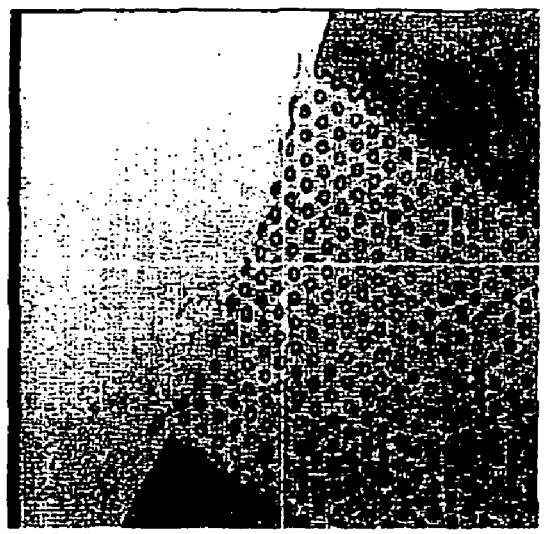
FIGS. 3A and 3B are explanatory drawings showing the protruding portions 13.
Figure 3B:
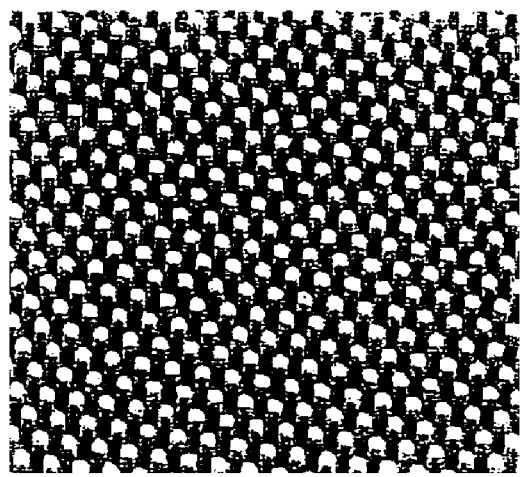

(A) First, the structure of the test apparatus of Working Example 1 will be explained with reference to FIGS. 1, 2A, 2B, 2C, 3A and 3B. Herein, FIG. 1 is a side view of part of the rotary member of the test apparatus. FIG. 2A is a plan view of a test object receptacle. FIG. 2B is a cross-sectional view in the A-A section in FIG. 2A. FIG. 3A is a photograph of some of the protruding portions formed inside the grooves of the test object receptacle, this photograph taken from above. FIG. 3B is a photograph of the protruding portions taken from the inclined direction.

The test apparatus 1, as shown in FIG. 1, is composed of a test object receptacle 3 composed of a polystyrene resin and a rotary member 5. The test object receptacle 3, as shown in FIGS. 2A, 2B and 2C, comprises a disk-like main body 7 with a diameter of 60 mm and a thickness of 2 mm, a liquid reservoir (central part, supply portion) 9 provided in the center of the upper surface 7a, which is the surface on one side of the main body 7, a plurality of grooves (supply sections) 11 formed radially from the outer periphery of the liquid reservoir 9 toward the outer peripheral end of the main body 7, and cylindrical protruding portions 13 raising vertically inside the grooves 11. A protrusion 9a is formed in the center of the liquid reservoir 9, a convex portion 9b, which is deeper than the groove 11, is formed around this protrusion 9a, and the test object (blood serum and the like) is supplied to this concave portion 9b. The concave portion 9b has a smooth continuous slope and is linked to the liquid reservoir 9 and grooves 11. The configuration is such that the amount of liquid necessary for the test is retained by this concave portion 9b.

The afore-mentioned grooves 11 have an almost rectangular cross section opened upward and are formed in the form of curved figures from the center of the main body 7 to the outer peripheral side thereof. The curve of the groove 11, as shown in FIG. 2A is such that the following Equation (1) is always satisfied for the angle θ between the straight line passing through points A and B and the tangent of L in B (that is, the advance direction of the groove 11 in B), wherein A is the center of the main body 7 and B is any point on the straight line L passing along the longitudinal direction of the groove 11 through the center thereof. Here, K is a constant, r is the distance between A and B, and ω is the angular speed at which the test object receptacle 3 attached to the rotary member 5 is caused to rotate.

$$\cos \theta = K/r\omega^2 \qquad \text{Equation (1)}$$

Further, the width of the groove 11 increases continuously toward the outer peripheral end of the main body 7, as shown in FIG. 2A, and the depth of the groove 11 increases continuously toward the outer peripheral end of the main body 7, as shown in FIG. 2B. The depth of the groove 11 is 0.3 mm in the vicinity of the inner peripheral edge of the main body 7 and 0.5 mm in the vicinity of the outer peripheral end thereof.

The outer peripheral end of groove 11 is open so that the test object pushed out by the centrifugal force can flow out of the groove. Furthermore, a liquid reservoir may be provided in the vicinity of the outer peripheral end of the groove 11 and the test object may be retained therein.

The afore-mentioned protruding portions 13 have a cylindrical shape with a diameter of 30 μm, as shown in FIG. 3, and are provided in a vertical condition in the upward direction (direction perpendicular to the upper surface 7a of the main body 7) on the bottom surface 11a of the groove 11.

The protruding portions 13 are regularly arranged with constant spacing over the entire surface of the bottom surface 11a of the groove 11, the pitch between the adjacent protruding portions 13 being 30 μm. Further, the width of the groove 11 increases as the outer peripheral end is approached, as was mentioned hereinabove, whereas the spacing between the protruding portions 13 is constant. Therefore, the number of protruding portions 13 contained per unit length of the groove 11 increases as the outer peripheral end of the groove 11 is approached. Furthermore, the protruding portions 13 and protrusion 9a are formed to have the same height, that is, so that the top ends thereof form the same horizontal plane. This configuration is suitable for the manufacture of the test object receptacle 3 by lithography.

The height of the protruding portions 13 matches the depth of the groove 11 in the position where the protruding portions 13 are formed. Therefore, the upper ends of the protruding portions 13 are in the same plane with the upper surfaces of the partitions 7b, which are the portions of the main body 7 where no grooves 11 are formed. Here, as described above, the depth of the groove 11 increases toward the outer periphery, and hence the height of the protruding portions 13 also increases toward the outer periphery of the main body 7. Accordingly, the surface area per one protruding portion 13 also increases toward the outer periphery of the main body 7.

In one of the partitions 7b serving as partitions separating the grooves 11 in the test object receptacle 3, a reference portion 14, which is a convex portion, is formed in the vicinity of the outer peripheral end thereof. This reference portion 14 is formed to have a different shape for each individual test object receptacle 3.

Figure 12:
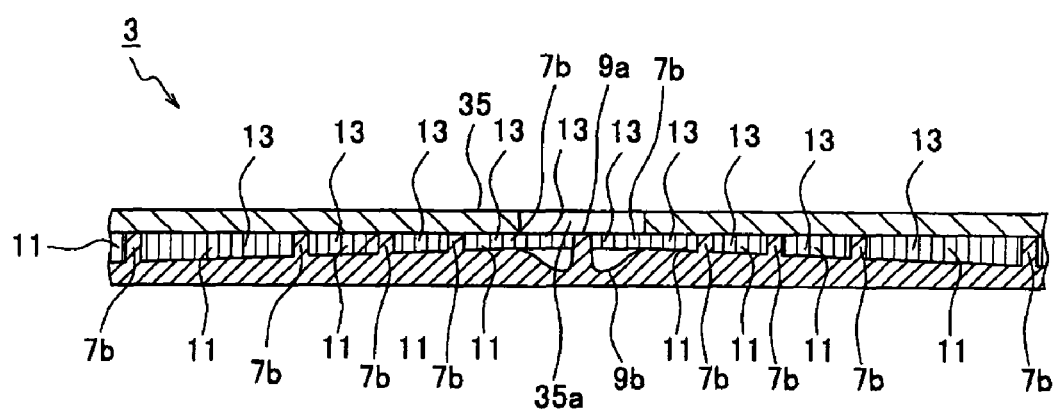
FIG. 12 is a cross-sectional view showing the configuration of the test object receptacle.

Further, the test object receptacle 3 has a cylindrical shape of the same size as the main body 7 and comprises a cover 35 with a hole 35a provided in the center thereof (see FIG. 12). This cover 35 is joined to the upper surface 7a of the main body 7. With this configuration, the hole 35a provided in the center of the cover 35 is positioned above the liquid reservoir 9. As a result, the test object can be supplied to the liquid reservoir 9 via the hole 35a. In the test object receptacle 3, the test object is prevented from leaking from the groove 11 by covering the groove 11 with the cover 35.

The rotary member 5 constituting the test apparatus 1, as shown in FIG. 1, comprises a chuck portion 15, a rotary shaft 17 attached to the center of the lower surface of the chuck portion 15, a rotation motor 19 for rotary driving the rotary shaft 17, and a bearing 21 for supporting the rotary shaft 17, and a cover portion 23 attached to the bearing 21. An opening (not shown in the figure) is formed in the upper surface of the chuck portion 15. This opening is linked to a suction pump (not shown in the figure), and the lower surface 7c of the main body 7 and the upper surface 15b of the chuck portion 15 are brought into intimate contact by the suction action of the suction pump, so that they cannot move with respect to each other. In other words, the chuck portion 15 and the test object 3 rotate integrally.

If the rotation motor 19 is driven in a state in which the test object receptacle 3 is fixed to the chuck portion 15, the test object receptacle 3 rotates about the rotation shaft 17 as a rotation center. At this time, the liquid reservoir 9 is positioned so as to become the rotation center for the test object receptacle 3.

(B) A method for the manufacture of the test object receptacle 3 of Working Example 1 will be described below.

First, a mold having a shape corresponding to that of the test object receptacle 3 is produced by using the well-known lithography technology. More specifically, first, a resist is coated on an electrically conductive substrate, a resist layer is formed, and the surface of the resist is covered with a mask provided with a slope gradient corresponding to the shape of the test object receptacle 3 and exposed to IR rays. Then, the exposed resist is developed and the developed resist is electroformed with a metal mold material. Finally, the resist and the substrate are removed to produce the metal mold.

The test object receptacle 3 is then manufactured by using an injection molding method. More specifically, a polystyrene resin is heated and melted inside a cylinder of the injection molding apparatus, then injected to fill the mold, and molded by cooling and solidification, thereby producing the test object receptacle 3.

Then, the test object receptacle 3 and a film having cut therein a portion corresponding to the upper surface of the liquid reservoir 9 and being a polystyrene film of the same material as the test object receptacle 3 are heated and joined to the upper surface 7a of the main body 7 to form a cover 35, thereby completing the manufacture of the test object receptacle 3. The material may be other resins, silicon rubbers or the like, provided that joining can be conducted. In addition to thermal bonding, joining of the cover 35 may be ultrasonic welding, joining with an adhesive, or pressure bonding, provided that the leak of the liquid from the grooves 11 is prevented.

(C) A test method using the test apparatus 1 of Working Example 1 will be explained below.

(i) Fixing an Antibody to the Test Object Receptacle 3

First, a total of 30 μL of a sodium carbonate buffer solution (0.05M, pH9.6, 100 μg/mL) of goat-derived transferrin antibody is poured into the grooves 11 of the test object receptacle 3. More specifically, the test object receptacle 3 is attached to the rotary member 5, as shown in FIG. 1, and the afore-mentioned sodium carbonate buffer solution of goat-derived transferrin antibody is injected into the liquid reservoir 9 located on the inner peripheral side of the grooves 11. The test object receptacle 3 is then rotated at a rotation speed of 150-15,000 rpm. As a result, the afore-mentioned solution supplied to the inner peripheral side of the grooves 11 flows through the grooves toward the outer periphery under the effect of a centrifugal force and reaches the outer peripheral end of grooves 11. Further, the end portions of the grooves 11 are open and connected to the outside of the test object receptacle 3. Therefore, the test object or reagent is discharged from this opening to the outside of the test object receptacle 3. The rotation of the test object receptacle 3 is then stopped. The above-described method is also used in the below-described processes even when other solutions or washing liquids are poured into the grooves 11.

After the sodium carbonate buffer solution of transferrin antibody has been removed from the grooves 11, 30 μL of a blocking solution (50 mM Tris, 0.14 M NaCl, 1% BSA, pH 8.0), is poured therein. In the previous process, the antibody is fixed to the surface of protruding portions 13 located inside the grooves 11. Then, the grooves 11 are washed twice by pouring a washing liquid (50 mM Tris, 0.14 M NaCl, 0.05% Tween 20, pH 8.0).

(ii) Entrapment of the Test Object by Antigen-Antibody Reaction

Here, transferrin serves as a test object. A total of 30 μL of a solution prepared by dissolving transferrin in a Tris buffer solution (50 mM Tris, 0.14 M NaCl, 1% BSA, 0.05% Tween 20, pH 8.0) to a concentration of 250 ng/mL is supplied to the inner peripheral side of the grooves 11 (first step). Then, the test object receptacle 3 is rotated at a rotation speed of 150-15,000 rpm, and the above-described solution supplied to the inner peripheral side of grooves 11 is caused to move to the outer peripheral end of grooves 11 (second step). The rotation of the test object receptacle 3 is then stopped. As a result of this process, the antibody fixed to the protruding portions 13 entraps the transferrin. Then, the grooves 11 are washed twice by pouring a washing liquid (50 mM Tris, 0.14 M NaCl, 0.05% Tween 20, pH 8.0).

(iii) Bonding of Labeled Antibody

A total of 30 μL of a solution prepared by dissolving a goat-derived HRP-labeled transferrin antibody in a Tris buffer solution (50 mM Tris, 0.14 M NaCl, 1% BSA, 0.05% Tween 20, pH 8.0) to a concentration of 500 ng/mL is poured into the grooves 11. In this process, the goat-derived transferrin antibody is joined by the antigen-antibody reaction to the transferrin that was entrapped in the above-described process (ii). Then, the grooves 11 are washed three times by pouring a washing liquid (50 mM Tris, 0.14 M NaCl, 0.05% Tween 20, pH 8.0).

(iv) Assay of the Test Object

A phosphoric acid—citric acid solution (0.05 M sodium phosphate, 0.05 M citric acid, 0.05% hydrogen peroxide) of ABTS is poured as a substrate solution into grooves 11 and transferrin, which is the test object, is caused to emit light.

Figure 4A:
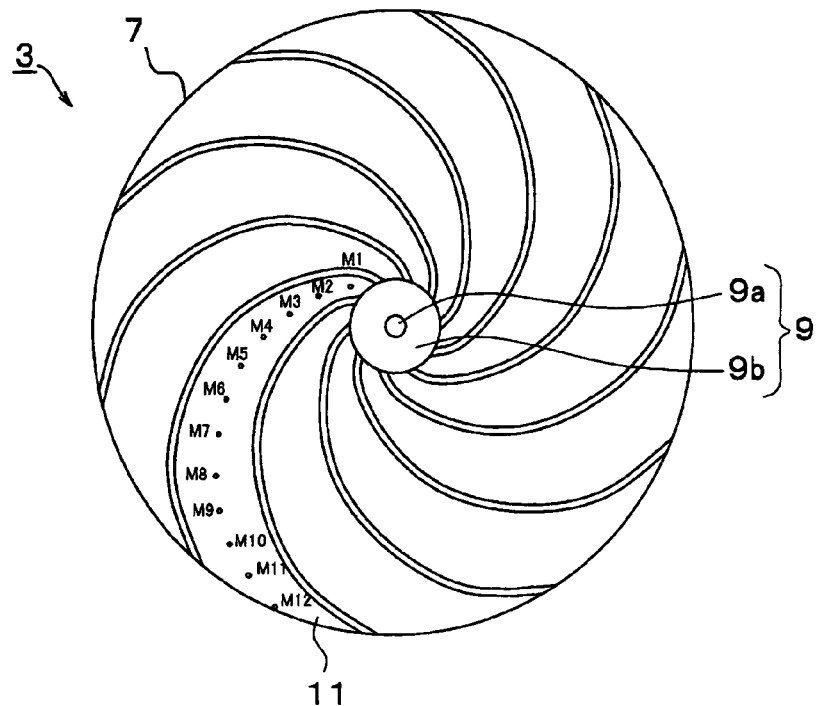
FIGS. 4A and 4B are explanatory drawings illustrating a test method using the test apparatus.
Figure 4B:
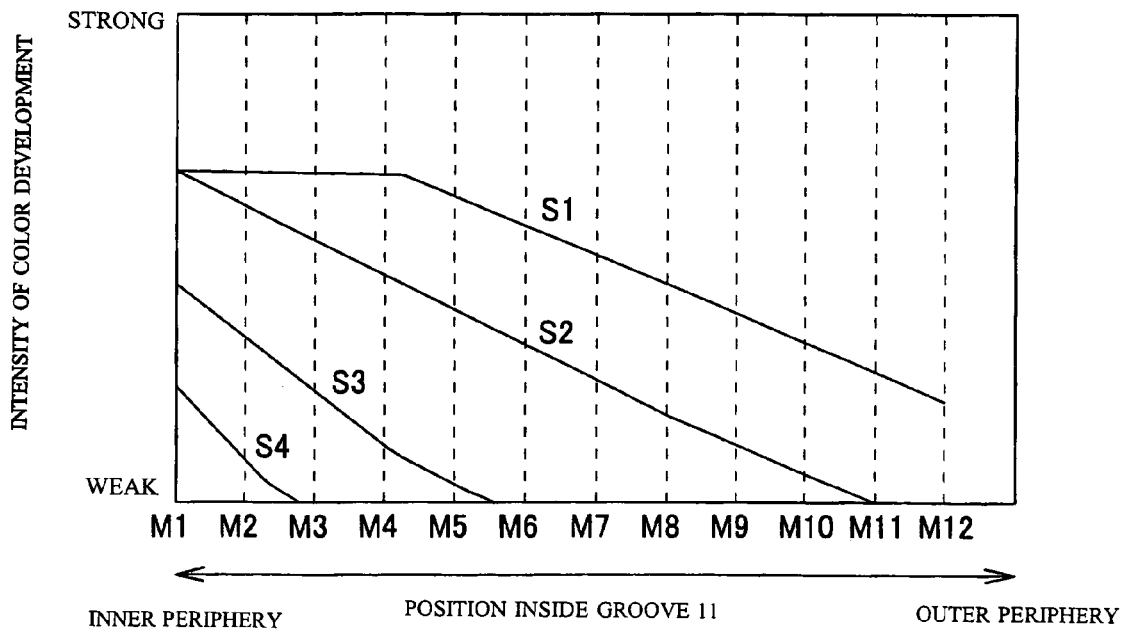

Then, as shown in FIG. 4A, images are picked up with a scanner in a plurality of positions M1 to M12 set from the inner peripheral side to the outer peripheral side of the groove 11 and the degree of color development is represented in numerical form with the darkness analysis software (third step). Then, the distribution of the degree (detected amount of the test object) of color development with respect to positions in the grooves 11 is computed. FIG. 4B is a graph showing this distribution and illustrating the relationship between the position inside the grooves 11 and the intensity of color development. Here, the curve (restriction line) in FIG. 4B changes correspondingly to the amount of the test object. In other words, when the amount of test object is large, the detected quantity reaches saturation on the inner peripheral side (for example, M1-4) and the detected quantity gradually decreases toward the outer peripheral side, as shown by curve S1 in the graph in FIG. 4B. As the quantity of the test object decreases, the curves successively change as S3, S2, S1. In those curves, there are no portions with saturated detection quantities and the detected quantity decreases gradually toward the outer peripheral side.

The test object is then assayed by using the graph plotted as shown in FIG. 4B. In other words, as shown in FIG. 5A, the surface area of a portion (hatched portion in FIG. 5A) is calculated, this portion being surrounded (bounded) by the restriction line showing the distribution with respect to the detected quantity of the test object, the abscissa (reference line relating to the distance in the supplied body) corresponding to the position in the groove 11, the line which is the ordinate corresponding to the intensity of the color development and passes through the initial point M1 of measurement (reference line relating to the detected quantity), and the line which is the ordinate corresponding to the intensity of the color development and passes through the final point M12 of measurement (reference line relating to the detected quantity).

Figure 5A:
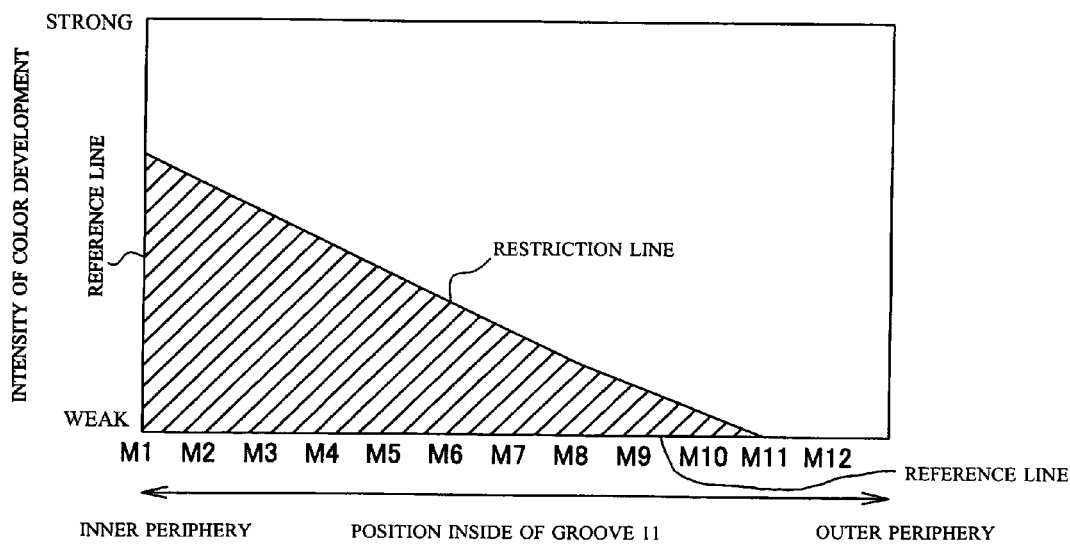
FIGS. 5A and 5B are explanatory drawings illustrating a test method using the test apparatus.

As shown in FIG. 5A, when no color development was detected in position M12, the delineated surface area becomes a surface area defined by a restriction curve representing the distribution relating to the detected quantity of the test object, an abscissa (reference line relating to the distance in the supply section) corresponding to the position in the groove 11, and an ordinate indicating the intensity of color development that is the line (reference line relating to the detected quantity) passing through the initial point M1 of measurements.

This surface area is then associated with the quantity of the test object and the test object is assayed. This surface area is a value obtained by integrating the intensity of color development (parameter corresponding to the quantity of test object) in each position in the groove 11 and, therefore, corresponds to the quantity of the test object.

Figure 5B:
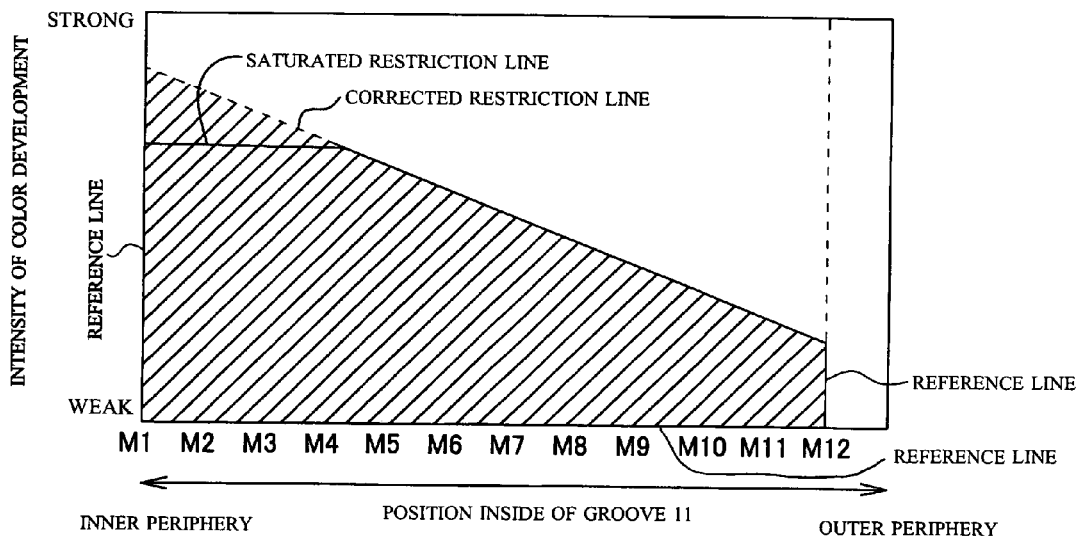

When the intensity of color development is saturated on the inner peripheral side of the groove 11, as shows by curve S1 in FIG. 4B, then extrapolation is conducted based on the portion of the curve where no saturation was reached, as shown in FIG. 5B, and the corrected restriction line relating to the case where the intensity of color development is not saturated is computed. Then, the surface area of the portion (hatched portion in FIG. 5B defined by this corrected restriction line, an abscissa corresponding to the position in the groove 11, an ordinate corresponding to the intensity of color development that is the line (reference line relating to the detected quantity) passing through the initial point M1 of measurements, and an ordinate corresponding to the intensity of color development that is the line (reference line relating to the detected quantity) passing through the final point M12 of measurements is computed and the test object is assayed by using this surface area.

(D) The effect demonstrated by the test object receptacle 3 and test apparatus 1 of Working Example 1 will be explained below.

(a) In the test object receptacle 3 of Working Example 1, protruding portions 13 with a surface area larger than that of the flat portion are provided inside the grooves 11. Therefore, if a test object is supplied into the grooves 11, the contact surface area of the test object and the protruding portions 13 is large and a large quantity of the test object can be adsorbed by the protruding portions 13. Therefore, if the test object receptacle 3 of Working Example 1 is used, the test object can be detected with good sensitivity.

(b) If the test object receptacle 3 of Working Example 1 is attached to the rotary member 5 and the test object receptacle 3 is rotated in a state that the test object has been supplied to the inner peripheral side of the grooves 11, then a centrifugal force acts upon the test object located inside the grooves 11, the test object is pushed out toward the outer periphery and moves, while colliding with the protruding portions 13. In this process the test object is effectively adsorbed by the protruding portions 13 due to collisions with the protruding portions 13. Therefore, with the test apparatus 1 of Working Example 1, the test object can be adsorbed by the test object receptacle 3 within a short time and the test can be conducted within a short time.

(c) In Working Example 1, because the supply section is the grooves 11, the test object is supplied into the grooves 11. Therefore, the reagent for detecting the test object may be coated only inside the grooves 11. As a result, the quantity of the reagent used can be reduced. Moreover, because the protruding portions 13 may be formed only inside the grooves 11, the test object receptacle 3 can be easily manufactured.

(d) In the test object receptacle 3 of Working Example 1, a plurality of grooves 11 are formed radially and the rotation center of the rotary member 5 is located in the center of radial grooves 11. Therefore, the centrifugal force is uniformly applied to the test object located in each groove 11. As a result, the detection of the test object in each groove 11 can be conducted under identical conditions.

(e) In Working Example 1, the protruding portions 13 were formed with a constant spacing inside the grooves 11 and the width of the grooves 11 increased toward the outer peripheral side (downstream side). For this reason, the number of protruding portions 13 contained per unit length of the grooves 11 increased toward the outer peripheral side and the surface area of the protruding portions 13 contained per unit length of the grooves 11 also increased toward the outer peripheral side. As a result, a larger quantity of the test object can be adsorbed by the protruding portions 13 on the outer peripheral side of the grooves 11 and even when the test object has a high concentration, it can be detected without dilution.

(f) In the grooves 11 of the test object receptacle 3 in Working Example 1, the depth of the grooves 11 increased toward the outer peripheral side and high protruding portions 13 were provided on the outer peripheral side where the grooves were deep. For this reason the surface per one protruding portion 13 increased toward the outer peripheral side and the surface area of the protruding portions 13 contained per unit length of the grooves 11 also increased toward the outer peripheral side. As a result, a large quantity of the test object can be adsorbed by the protruding portions 13 on the outer peripheral side of the grooves 11 and even when the test object has a high concentration, it can be detected without dilution.

(g) In Working Example 1, the height of the protruding portions 13 of the test object receptacle 3 was directly proportional to the depth of the grooves 11 in the location of the protruding portions 13. Therefore, the height of the protruding portions 13 can reach the upper side of the groove 11 correspondingly to the depth of groove 11. As a result, the test object cannot move over the top of protruding portions 13 and hence the test object can be adsorbed by the protruding portions 13 with good efficiency. As a result, the test object can be accurately detected.

Further, the protruding portions 13 cannot protrude to the outside of the grooves 11 correspondingly to the depth of the grooves 11. Therefore, the grooves 11 can be covered with a lid. As a result, spillage of the test object out of the grooves 11 can be prevented.

(h) In Working Example 1, as described hereinabove, the grooves 11 are formed along the curves such that the above-described Equation (1) is always valid for the angle θ between the straight line passing through points A and B and the tangent of L in B, where A is the center of the main body 7 (that is, the rotation center of the rotary member 5) and B is any point on the straight line L passing through the center of the groove 11.

If the grooves 11 are thus formed, of the centrifugal force acting upon the test object located inside the grooves 11, the component acting in the forward direction of the grooves is always constant, regardless of the distance between the points A and B. Therefore, the movement speed of the test object moving inside the grooves 11 with respect to the grooves 11 is always constant. As a result, the prescribed quantity of the test object adsorbed in each position M1 to M12 in the grooves 11 can be always obtained. Therefore, the quantity of the test object in each position M1 to M12 can be accurately detected and the test object can be assayed with good accuracy.

(i) The test object receptacle 3 of Working Example 1 has a disk-like main body 7. Therefore, it can be easily manufactured by a method using a mold. Furthermore, because the main body 7 has a disk-like shape, a centrifugal force can be easily applied to the test object located inside the grooves and the test object can be moved with a high speed when the disk is rotated. As a result, if the test object receptacle 3 of Working Example 1 is used, the time required for the test can be shortened. Moreover, because the main body 7 has a disk-like shape, there is no dead space where the grooves 11 cannot be formed. Therefore, the amount of resin constituting the main body 7 can be reduced. As a result, the size and weight of the test object receptacle 3 of Working Example 1 can be reduced and the production cost can be lowered.

(j) In the test object receptacle 3 of Working Example 1, the protruding portions 13 had a cylindrical shape and the protruding portions 13 were formed integrally with the grooves 11. Therefore, the protruding portions 13 can be processed within a short time and can be easily manufactured.

(k) In Working Example 1, the spacing between the protruding portions 13 was 8 µm or less. Therefore, the protruding portions 13 can function as a filter and can remove, for example, neutrophilic leucocytes, acidophilic leucocytes, basophilic leucocytes, and monocytes of white corpuscles which are larger than 8 µm. Furthermore, because the spacing between the protruding portions 13 is 2 µm or more, smaller portions cannot be clogged.

The spacing between the protruding portions 13 also may be 0.3-2 µm. In this case, the protruding portions 13 also function as a filter and can remove, for example, red corpuscles, white corpuscles engulfing foreign matter, blood platelets, and corpuscles which are larger than 2 µm. Furthermore, because the spacing between the protruding portions 13 is 0.3 µm or more, smaller portions cannot be clogged.

(l) In the test object receptacle 3 of Working Example 1, a reference portion 14 is provided as shown in FIG. 2, and the shape of the reference portion 14 differs for each test object receptacle 3. Therefore, even when a plurality of test object receptacles 3 are used by attaching to the rotary member 5, the specific test object receptacle 3 can be easily distinguished based on the reference portion 14. Further, when the test object receptacle 3 is rotated, each groove 11 can be distinguished based on the position of the reference portion 14. Because the reference portion 14 is formed integrally with the test object receptacle 3, the reference portion 14 can be easily formed.

(E) The effect demonstrated by the test method using the test apparatus 1 of Working Example 1 will be described below.

(a) In Working Example 1, as shown in FIGS. 5A and 5B, the test object is assayed based on the surface area defined by the reference line and restriction line showing the detected quantity in each position M1 to M12 inside the grooves 11. Therefore, the range in which the concentration of the test object can be measured has a large width.

In other words, for example, if the intensity of color development is to be detected only in the position M1 inside the groove 11, then when the concentration of the test object is high, as shown by the restriction line S1 or S2 in FIG. 4B, the intensity of color development reaches saturation in the position M1 and the test object cannot be assayed. Furthermore, if the intensity of color development is to be detected only in the position M12, then when the concentration of the test object is low, as shown by the restriction lines S2 to S4 in FIG. 4B, color development cannot be detected in the position M12, and the test object cannot be assayed.

By contrast, with the test method of Working Example 1, color development is detected in each point of positions M1 to M12. Therefore, even when the concentration of the test object is high (restriction line S1 in FIG. 4B) or when the concentration of the test object is low (restriction line S4 in FIG. 4B), the test object can be assayed.

(b) In Working Example 1, when the intensity of color development (detected quantity) is saturated in some of the restriction lines, as shown by the restriction line S1 in FIG. 4B), the corrected restriction line without the saturation is computed by extrapolation and the surface area is delineated by using this corrected restriction line. For this reason, even when the intensity of color development is saturated in some of the restriction lines, the test object can be assayed with good accuracy.

Working Example 2

The configuration of the test apparatus 1 of Working Example 2 is basically identical to that of Working Example 1, but the configuration of the test object receptacle 3 is somewhat different. The explanation given below with reference to FIG. 6 will be focused on this difference.

Figure 6A:
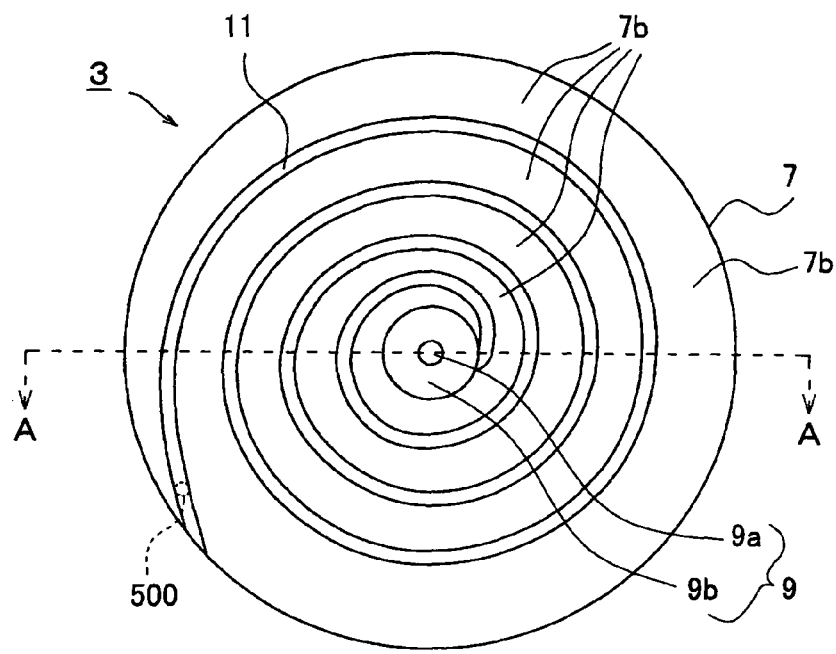
FIG. 6A is a plan view showing the configuration of the test object receptacle.
Figure 6B:
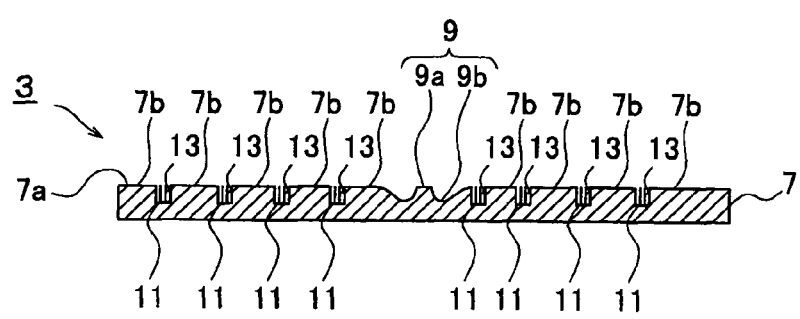
FIG. 6B is the cross-sectional view taken along the line A-A.

A test object receptacle 3, as shown in FIG. 6A has one spiral groove 11 on the upper surface 7a of a main body 7, this groove passing from a central hole 9 to the outer peripheral edge of the main body 7. The width of the groove 11 is constant from the inner peripheral side to the outer peripheral side of the main body 7 and the depth of the groove 11 is constant, as shown in FIG. 6B.

The test apparatus 1 of Working Example 2 can be used similarly to the test apparatus 1 of Working Example 1 and produces the same effect. Furthermore, in the test apparatus 1 of Working Example 2, the groove 11 of the test object receptacle 3 is especially long. Therefore, the test object can be detected along a large distance. Therefore, the detectability range of the test object can be further expanded.

Working Example 3

The configuration of the test apparatus 1 of Working Example 3 is basically identical to that of Working Example 1, but the configuration of the test object receptacle 3 is somewhat different. The explanation given below with reference to FIGS. 7A and 7B will be focused on this difference.

In Working Example 3, in addition to protruding portions 13a identical to the protruding portions in Working Example 1 described hereinabove, protruding portions 13b formed integrally with the side surfaces 11b are provided in the groove 11 of the test object receptacle 3, as shown in FIG. 7A. Those protruding portions 13b have a shape obtained by dividing the protruding portion 13a in two equal parts by a plane along the longitudinal direction thereof. In the protruding portions 13b, a semispherical bottom surface 13b-1 is on the bottom surface 11a of the groove 11 and the rectangular cross section 13b-2 is on the side surface 11b of the groove 11. Further, the longitudinal direction of the protruding portions 13b is the same as the protrusion direction of the protruding portions 13a and the height, h, thereof is the same as the height of the protruding portions 13a.

The test apparatus 1 of Working Example 3 can be used similarly to the test apparatus 1 of Working Example 1 and produces the same effect. Further, in Working Example 3, the protruding portions 13b, which are some of protruding portions 13, are formed integrally with the side surface 11b of the groove 11. Therefore, by contrast with the case where the protruding portions 13b are not provided, there is no risk of the test object preferentially flowing through both ends of the groove 11 that comprise no protruding portions 13b. In addition, the adsorption can be conducted with better efficiency than in the case where no protruding portions 13b are provided.

Working Example 4

Figure 8:
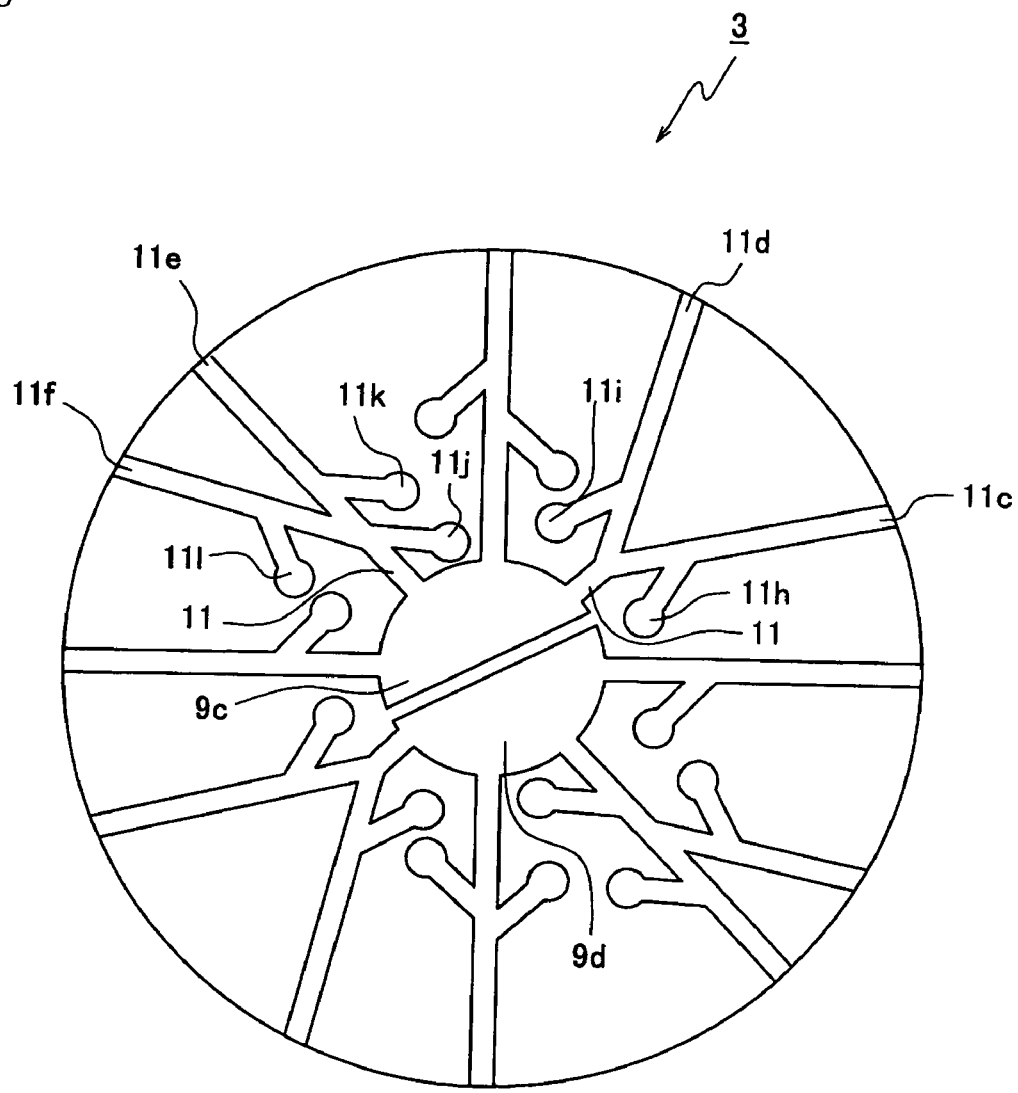
FIG. 8 is a plan view showing the configuration of the test object receptacle.

The configuration of the test apparatus 1 of Working Example 4 is basically identical to that of Working Example 1, but the configuration of the test object receptacle 3 is somewhat different. The explanation given below with reference to FIG. 8 will be focused on this difference.

In the test object receptacle 3 of Working Example 4, the liquid reservoir 9 has two individual concave portions 9c, 9d. Some of the grooves 11 linked to the convex portion 9c are branched into a groove 11c and a groove 11d as a transition is made in the direction toward the outer periphery. The liquid reservoir 11h into which a reagent is introduced is linked to the groove 11c on the side close to the center (shifted toward the center) of the groove 11c. Similarly, the liquid reservoir 11i is linked to the groove 11d on the side close to the center (shifted toward the center) of the groove 11d.

As a result, introducing different test reagents into the liquid reservoirs 11h and 11j makes it possible to conduct test measurements of two types at the same time from the same specimen of the liquid reservoir 9c. In other words, the test object supplied into the liquid reservoir 9c is divided into the portion flowing into the groove 11c and a portion flowing into the groove 11d. Therefore, in the test object flowing in the groove 11c, the test measurements can be conducted by using the reagent supplied from the liquid reservoir 11h, and in the test object flowing in the groove 11d, the test measurements can be conducted by using a reagent supplied from the liquid reservoir 11i, this reagent being different from the reagent supplied into the liquid reservoir 11h. Thus, a plurality of tests can be conducted at the same time from the same specimen of the liquid reservoir 9c.

Furthermore, another groove 11 linked to the convex portion 9c is divided into a groove 11e and a groove 11f, and the liquid reservoir 11j is linked to this groove 11 before the branching point. As a result, the reagent can be supplied from the liquid reservoir 11j to the test object before the groove is branched into the groove 11e and groove 11f.

The groove 11 linked to the liquid reservoir 9d is formed similarly to the groove 11 linked to the liquid reservoir 9c. As a result, the tests of other types or multiple types can be conducted simultaneously from a plurality of test bodies. For example, blood serum samples (test objects) of different people can be supplied into liquid reservoirs 9c and 9d and test measurement can be conducted simultaneously with respect to those blood serum samples. Thus, the arrangement of grooves and liquid reservoirs may be optionally designed according to the test method.

Working Example 5

The configuration of the test apparatus 1 of Working Example 5 is basically identical to that of Working Example 1, but the configuration of the test object receptacle 3 is somewhat different. The explanation given below with reference to FIG. 9 will be focused on this difference.

Figure 9:
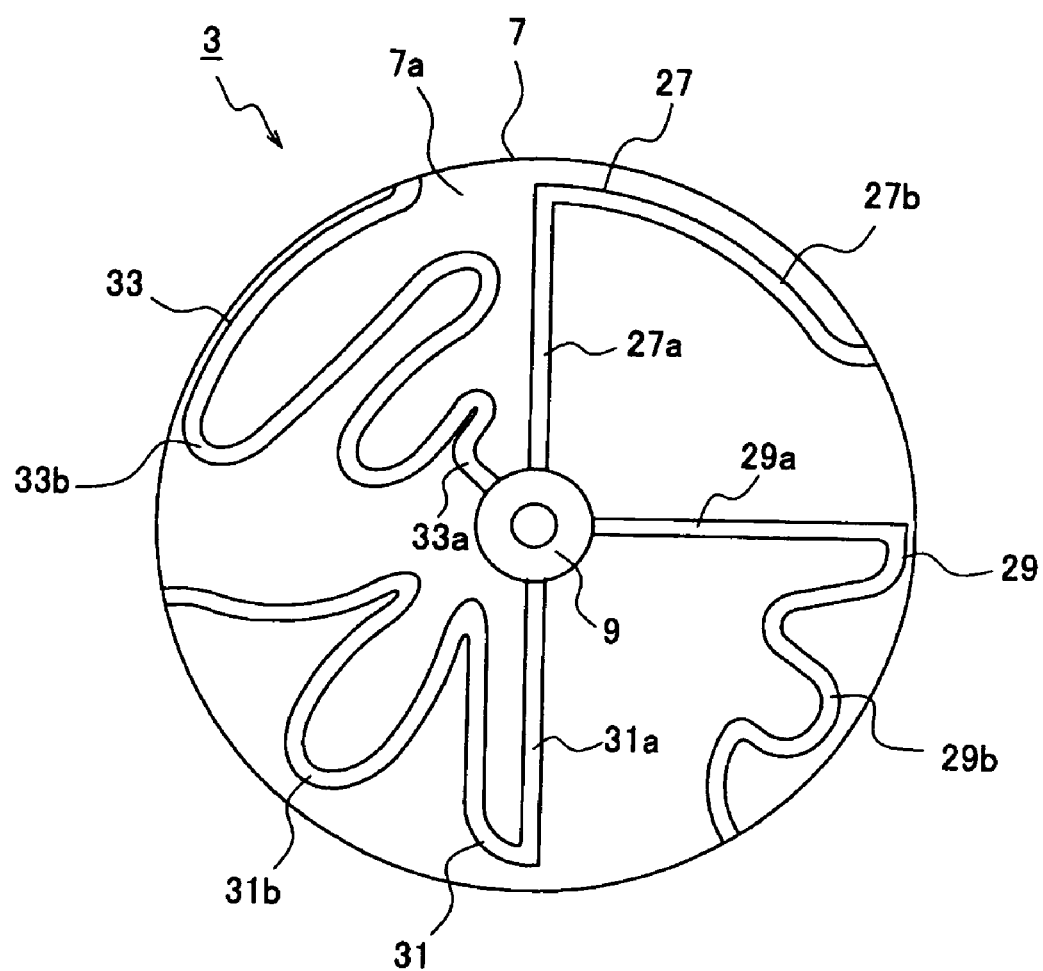
FIG. 9 is a plan view showing the configuration of the test object receptacle.

In the test object receptacle 3 of Working Example 5, as shown in FIG. 9, a groove 27, a groove 29, a groove 31, and a groove 33 with a rectangular cross section open at the top are provided in the upper surface 7a of the main body 7. In the bottom surfaces of those grooves 27, 29, 31, and 33, protruding portions 13 are provided in the same manner in which protruding portions 13 were provided in the bottom surface 11a of the groove 11 in Working Example 1.

The groove 27 is composed of a radial portion 27a extending from the liquid reservoir 9 in the radial direction of the test object receptacle 3 (the direction that becomes radial direction in rotation of the rotary shaft 17 when the test object receptacle is attached to the rotary member 5) and a circumferential portion 27b extending in the circumferential direction of the test object receptacle 3 (the direction that becomes circumferential direction in rotation of the rotary shaft 17 when the test object receptacle is attached to the rotary member 5) in the zone downstream of the radial portion 27a.

The groove 29 is composed, as shown in FIG. 9, of a radial portion 29a extending from the liquid reservoir 9 in the radial direction of the test object receptacle 3 and a meandering portion 29b located downstream of the radial portion 29a.

Further, as shown in FIG. 9, the groove 31 is also composed of a radial portion 31a extending from the liquid reservoir 9 in the radial direction of test object receptacle 3 and a meandering portion 31b located downstream of the radial portion 31a. The groove 33 is also composed of a radial portion 33a extending from the central hole 9 in the radial direction of test object receptacle 3 and a meandering portion 33b located downstream of the radial portion 33a. In the groove 29 and groove 31, the oscillation direction of the meandering path is the radial direction of the test object receptacle 3, whereas in the groove 33, the oscillation direction of the meandering path is in the circumferential direction of the test object receptacle 3. Furthermore, the radial portion 29a of the groove 29 and the radial portion 31a of the groove 31 have a length which is almost the radial length of the test object receptacle 3, but the length of the radial portion 33a of the groove 33 is about ⅓ of the radial length of the test object receptacle 3.

The grooves 27, 29, 31, 33 in Working Example 5 have a circumferential portion or meandering portion in addition to the radial portion. Therefore, the total length thereof is large. As a result, the adsorbed quantity of the test object can be increased and the test object can be detected with high sensitivity.

Working Example 6

The configuration of the test apparatus 1 of Working Example 6 is basically identical to that of Working Example 1, but the configuration of the test object receptacle 3 is somewhat different. The explanation given below with reference to FIG. 10 will be focused on this difference. Here, FIG. 10A is a plan view representing the test object receptacle 3, and FIG. 10B is a cross-sectional view along the line A-A in FIG. 10A.

Figure 10A:
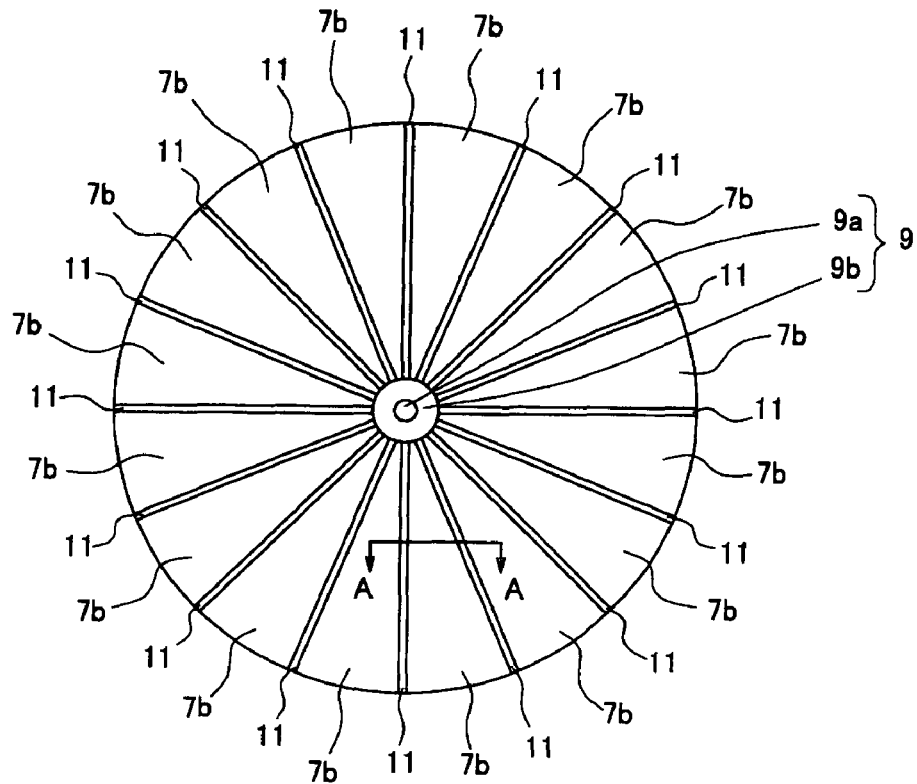
FIG. 10A is a plan view showing the configuration of the test object receptacle.
Figure 10B:
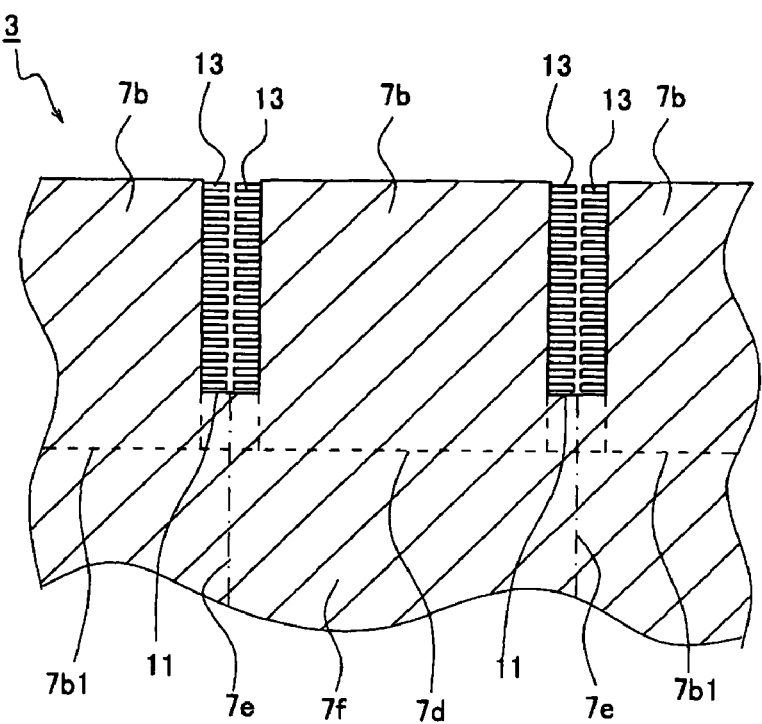
FIG. 10B is the cross-sectional view taken along the line A-A.

In the test object receptacle 3 of Working Example 6, as shown in FIG. 10A, the grooves 11 extend linearly from the liquid reservoir 9 to the outer periphery and the width of the grooves 11 is narrower than the width of partitions 7b. Further, as shown in FIG. 10B, protruding portions 13 are formed in the side walls 11b of the grooves 11. The protruding portions 13 in Working Example 6 have a cylindrical shape, and the protrusion direction thereof is perpendicular to the side walls 11b of the grooves 11 and parallel to the bottom surfaces 11a. Further, the size of protruding portions 13 or the arrangement and mutual spacing of protruding portions 13 are identical to those of Working Example 1.

The main body 7 of the test object receptacle 3 in Working Example 6 may be manufactured by manufacturing separately at least two parts and then assembling those parts. For example, in the manufacture of the main body 7, the partitions 7b can be separately manufactured by setting the dot line 7d shown in FIG. 10B as a boundary line and then inserting the partitions into the main body 7 (portion without the partitions 7b). Alternatively, the parts may be manufactured by setting a dash-dot line 7e shown in FIG. 10B as a boundary line and then the main body 7 may be manufactured by joining those parts. The problem of poor separation from the mold when the main body 7 is manufactured can be resolved by using the above-described methods.

Figure 11:
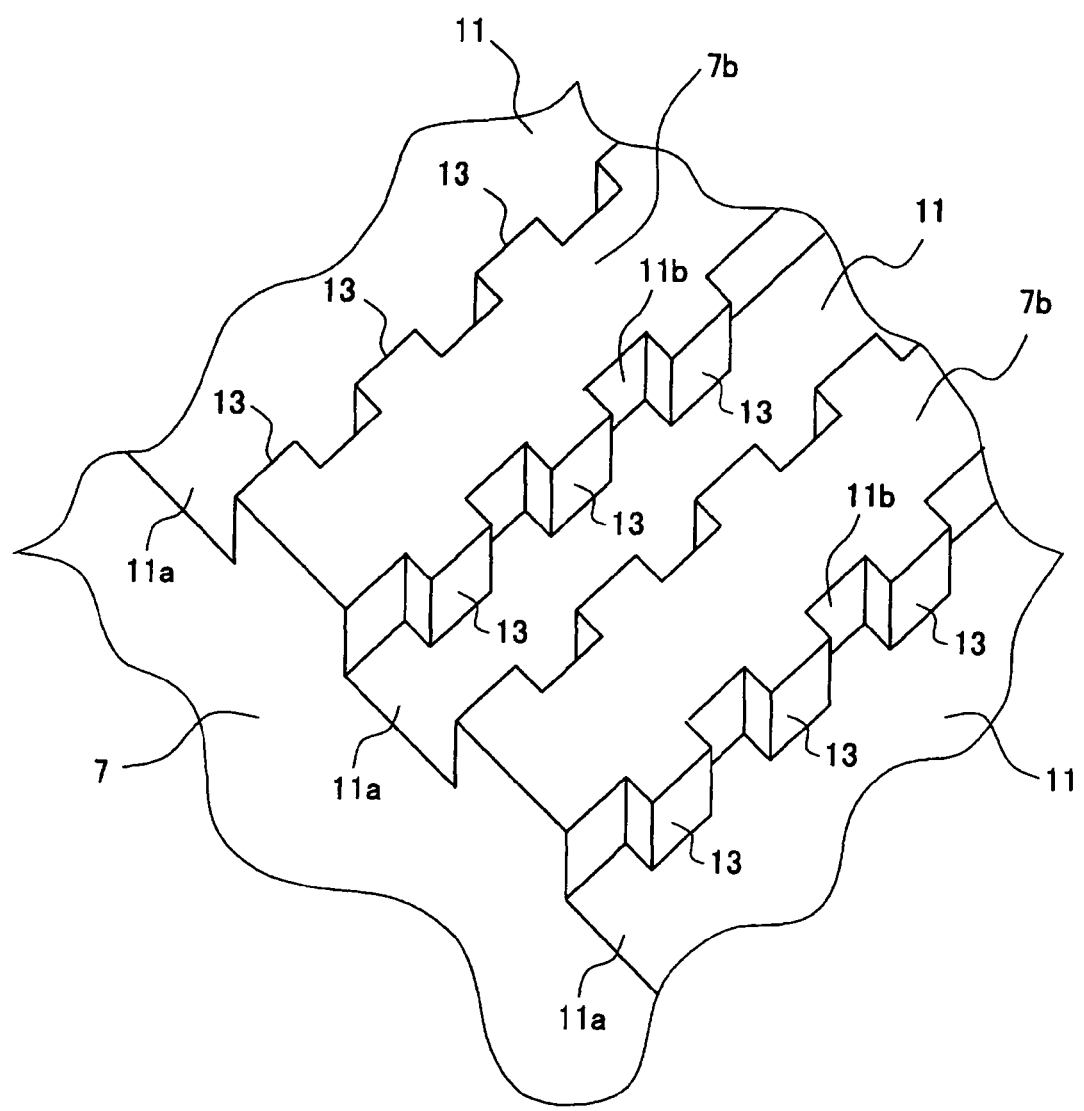
FIG. 11 is a perspective view showing the configuration of the test object receptacle.

The protruding portions 13 in Working Example 6 may have the shape of rectangular parallelepipeds protruding from the side surfaces 11b of the grooves 11, as shown in FIG. 11.

Further, in Working Example 7 the protruding portions 13 may be formed on the side surfaces 11b of the grooves 11 and the protruding portions 13 may be also formed on the bottom surfaces 11a of the grooves 11, similarly to Working Example 1.

Working Example 7

The configuration of the test apparatus 1 of Working Example 7 is basically identical to that of Working Example 1, but the configuration of the test object receptacle 3 is somewhat different. The explanation given below with reference to FIGS. 12, 13A, 13B and 13C will be focused on this difference.

Figure 13A:
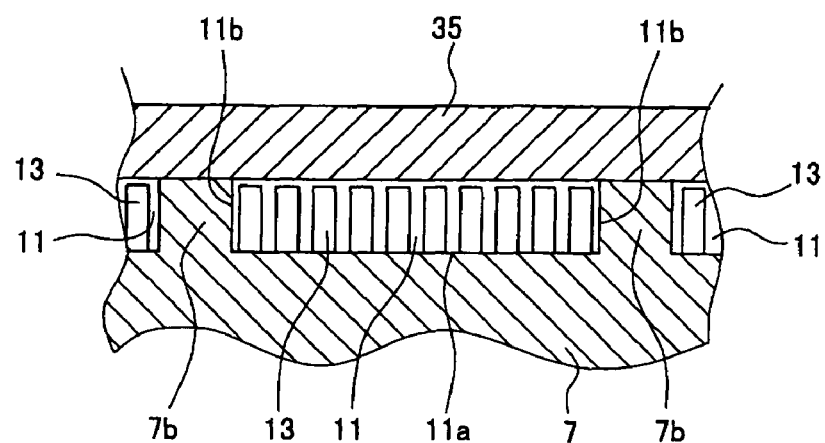
FIGS. 13A, 13B and 13C are cross-sectional views showing the configuration of the test object receptacle.

The test object receptacle 3 as shown in FIG. 12, comprises a lid 35 that can cover the upper surface 7a of the main body 7. This lid 35 has a disk-like shape and the same diameter as the main body 7. When the lid 35 is attached, as shown in FIG. 13A, the openings in the upper part of the grooves 11 of the test object receptacle 3 are closed with the lid 35.

Figure 13B:
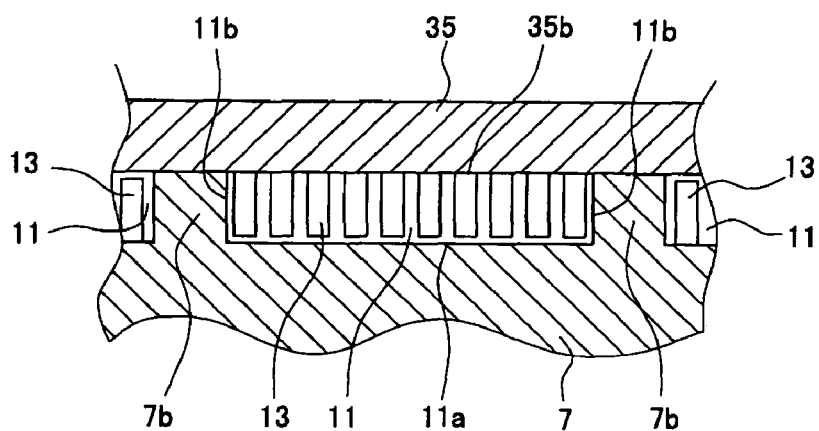

In Working Example 7, instead of forming the protruding portions 13 in the bottom surfaces 11a of the grooves 11, they may be formed so as to protrude downward from the bottom surface 35b of the lid 35, as shown in FIG. 13B. In this case, the protruding portions 13 are provided in locations such that they are introduced into the grooves 11 when the lid 35 is attached to the main body 7. Furthermore, the height of the protruding portions 13 can be such that the distal ends of the protruding portions 13 reach the vicinity of the bottom surfaces 11a of the grooves 11 when the lid 35 is attached to the main body 7. The shape and diameter of protruding portions 13 and mutual spacing of the protruding portions 13 can be identical to those of Working Example 1.

Figure 13C:
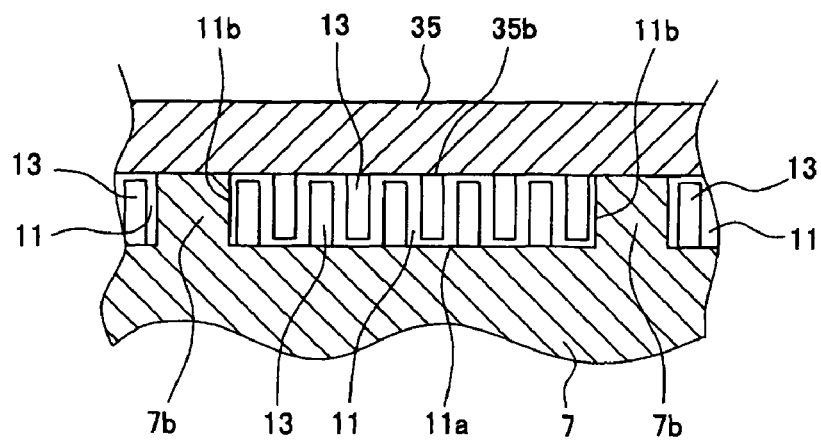

Further, the protruding portions 13 may be formed so as to protrude upward from the bottom surfaces 11a of the grooves 11, as shown in FIG. 13C and they may also protrude downward from the lower surface 35b of the lid 35.

With the test object receptacle 3 of Working Example 7, when a biological material or reagent is supplied into the grooves 11, the lid 35 is removed, and when the test object receptacle 3 is rotated, the lid 35 can be attached. As a result, when the test object receptacle 3 is rotated, the biological material or reagent are prevented from scattering. Furthermore, a supply orifice 35a for supplying the biological material or reagent may be provided in the lid 35, for example, above the liquid reservoir 9.

Working Example 8

The configuration of the test apparatus 1 of Working Example 8 is basically identical to that of Working Example 1, but the configuration of the test object receptacle 3 is somewhat different. The explanation given below with reference to FIGS. 14A and 14B will be focused on this difference. Here, FIG. 14A is a plan view representing the test object receptacle 3, and FIG. 14B is a cross-sectional view along the line A-A in FIG. 14A.

Figure 14A:
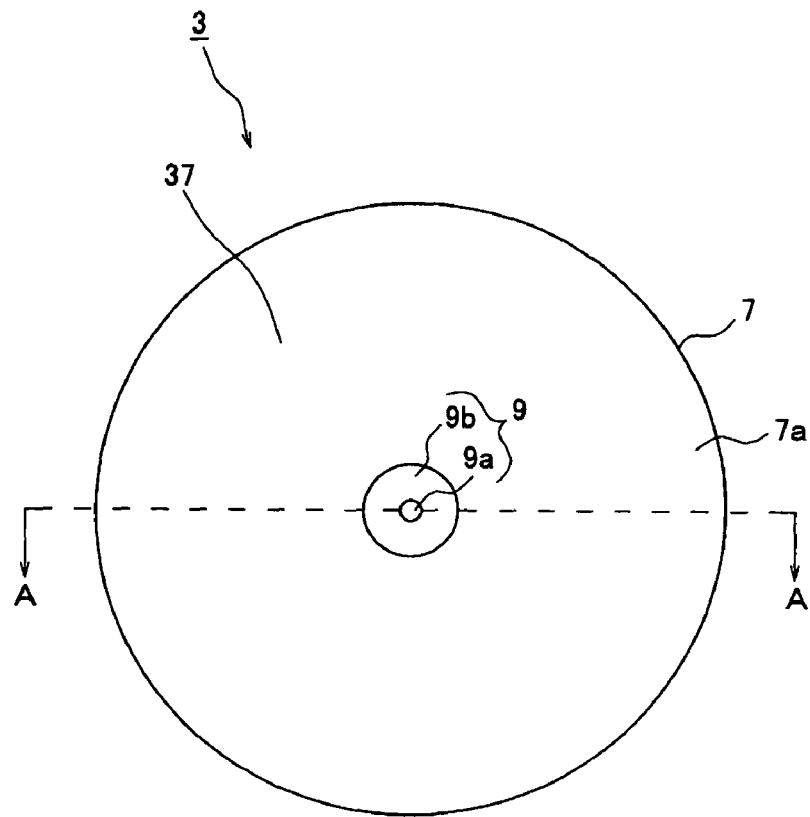
FIG. 14A is a plan view showing the configuration of the test object receptacle.
Figure 14B:
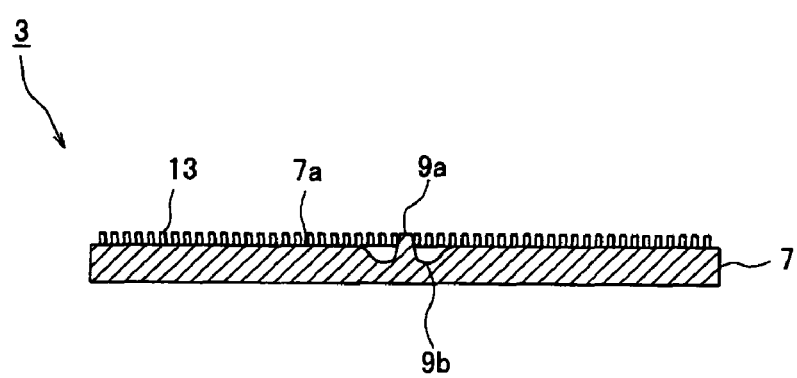
FIG. 14B is the cross-sectional view taken along the line A-A.

In Working Example 8, as shown in FIG. 14A, the upper surface 7a of the disk-like main body 7 constituting the test object receptacle 3 is composed of a liquid reservoir 9 and a supply section 37 which is the entire region except the liquid reservoir 9. As shown in FIG. 14B, the protruding portions 13 are formed over the entire supply section 37. The shape, size, and arrangement pattern of the protruding portions 13 and the mutual spacing of the protruding portions 13 are identical to those of the protruding portions 13 formed in the grooves 11 in Working Example 1. Furthermore, the height of the protruding portions 13 can be the same over the entire supply section 37.

Working Example 9

The configuration of the test apparatus 1 of Working Example 9 is basically identical to that of Working Example 1, but the configuration of the test object receptacle 3 is somewhat different. The explanation given below with reference to FIGS. 15A, 15B and 15C will be focused on this difference. Here, FIG. 15A is a plan view representing the test object receptacle 3, and FIGS. 15B and 15C are cross-sectional views along the line A-A in FIG. 15A.

Figure 15A:
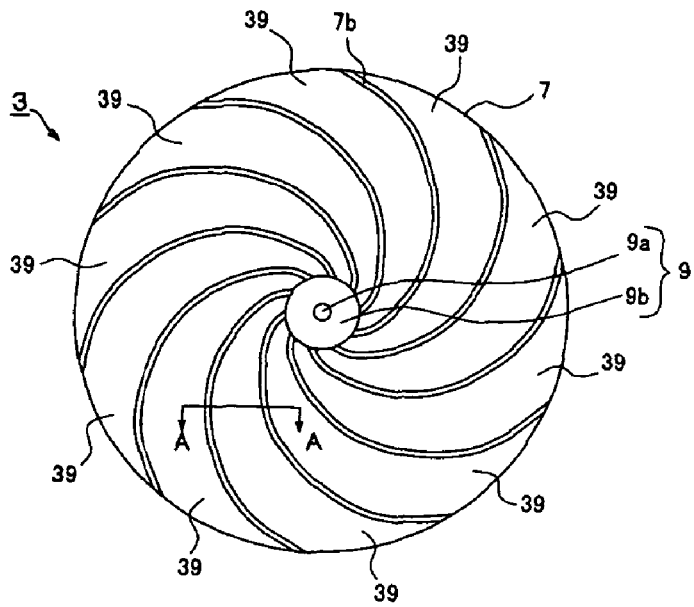
FIG. 15A is a plan view showing the configuration of the test object receptacle.
Figure 15B:
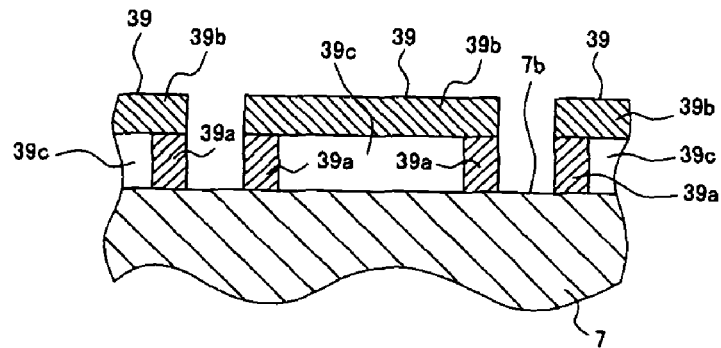
FIGS. 15B and 15C are the cross-sectional views taken along the line A-A.

In the test object receptacle 3 of Working Example 9, supply sections 39 shown in FIG. 15A are formed instead of the grooves 11. The supply section 39 is composed of a pair of partitions 39a provided vertically on the upper surface 7a of the main body 7 and a plate-like lid 39b attached to the upper portion of the pair of partitions 39a. A biological material or reagent passes through a passage 39c defined by the partitions 39a and lid 39b.

Figure 15C:
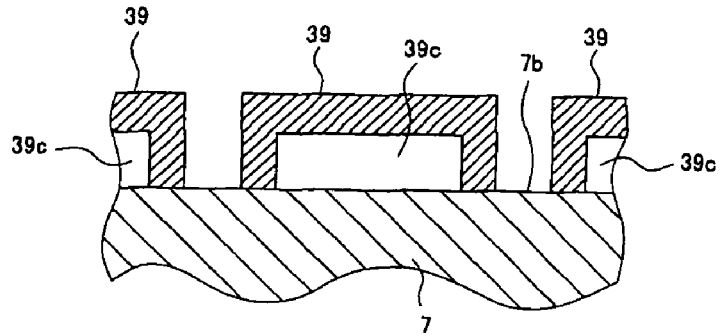

The supply section 39 in Working Example 9 may be formed by attaching a member with a U-like cross section having a downward opening to the upper surface 7a of the main body 7, as shown in FIG. 15C.

As a result, when the test object receptacle 3 is rotated, the biological material or reagent are prevented from scattering. Furthermore, a supply orifice for supplying the biological material or reagent may be provided in the lid 39b.

Working Example 10

The configuration of the test apparatus 1 of Working Example 10 is basically identical to that of Working Example 1, but the configuration of the test object receptacle 3 is somewhat different. The explanation given below with reference to FIGS. 16A and 16B will be focused on this difference.

Figure 16A:
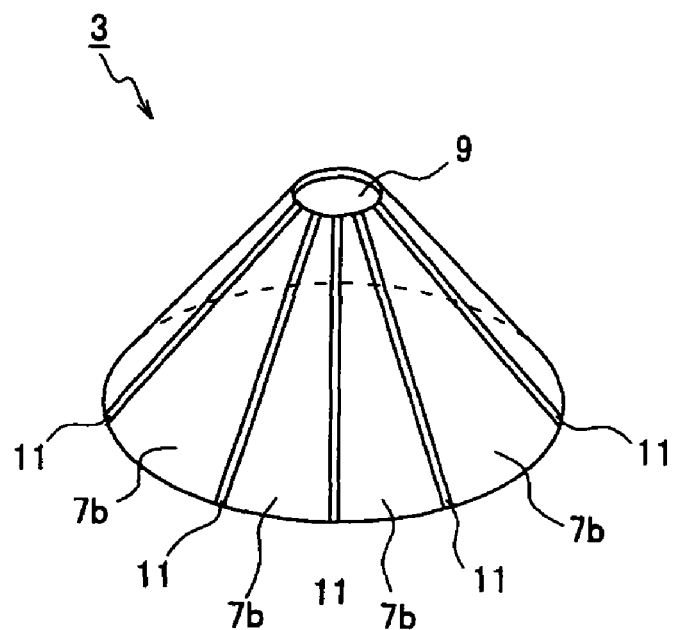
FIGS. 16A and 16B are perspective views showing the configuration of the test object receptacle.

In Working Example 10, as shown in FIG. 16A, the main body 7 of the test object receptacle 3 has a conical shape, and a liquid reservoir 9 is formed in the apex of the cone. Further, grooves 11 extend linearly toward the outer periphery from the liquid reservoir 9 over the side surface of the cone. Here, the grooves 11 have a lowering gradient in the direction from the liquid reservoir 9 to the outer periphery.

Figure 16B:
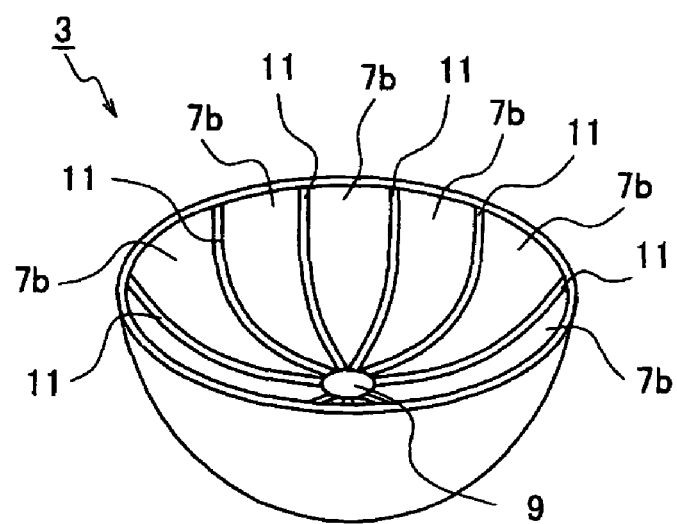
Figure 17A:
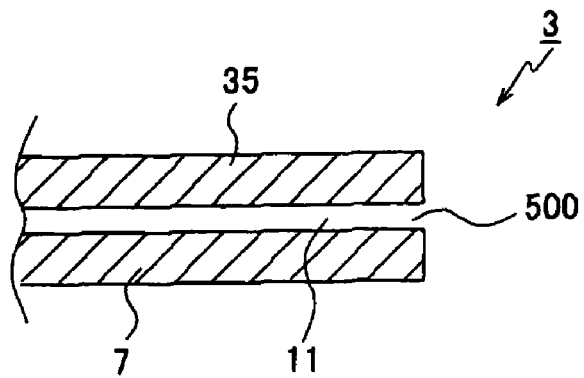
FIGS. 17A, 17B, 17C and 17D are side sectional views showing the configuration of the grooves in the test object receptacle.
Figure 17B:
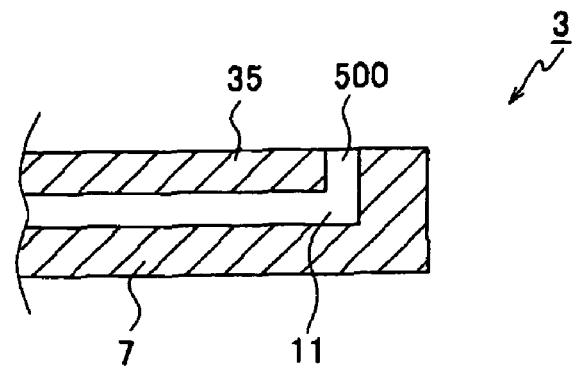
Figure 17C:
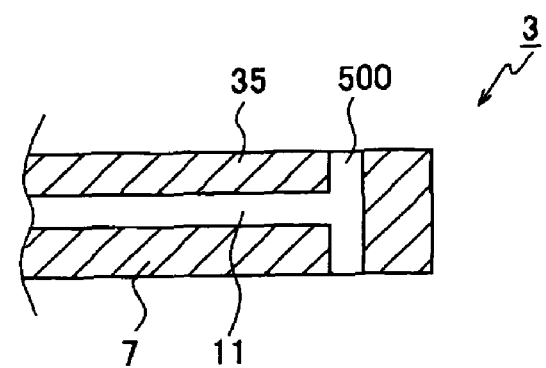
Figure 17D:
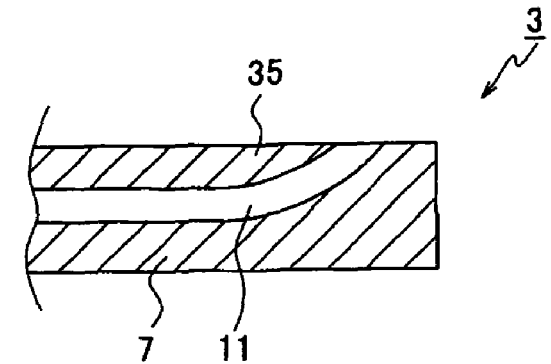

Furthermore, in Working Example 10, the main body 7 may have a semispherical shape with a concave cross section, as shown in FIG. 16B. The liquid reservoir 9 is formed in the center of the concave portion, and the grooves 11 extend from the liquid reservoir 9 linearly toward the outer periphery along the inner surface of the semisphere. The grooves 11 have a rising gradient in the direction from the liquid reservoir 9 to the outer periphery.

In Working Example 10, the test object receptacle 3 has a three-dimensional shape, as shown in FIGS. 16A and 16B. Therefore, a chuck 15 for fixing the test object receptacle 3 (see FIG. 1) has a shape corresponding to this three-dimensional shape.

The present invention is not limited in any way to the above-described working examples, and it goes without saying that it can be implemented in a variety of modes without departing from the scope thereof.

For example, in the above-described working examples, the depth of the grooves 11 may be constant from the inner peripheral side to the outer peripheral side of the test object receptacle. In this case, the depth of the test object present inside the grooves 11 is also constant. Therefore, when the test object is detected by using transmission light, the test object can be accurately detected.

Furthermore, in the above-described working examples, the thickness of the bottom portion of the main body 7 of the test object receptacle 3 (thickness from the bottom surface 11a of the groove 11 to the lower surface 7c of the main body 7) may be constant from the inner periphery to the outer periphery, as shown in FIG. 2C.

Further, in the above-described working examples, the height of the protruding portions 13 may be constant, regardless of the position inside the grooves 11 and the surface area per one protruding portion 13 may be also constant.

Furthermore, in the above-described working examples, the protruding portions 13 may protrude in the direction perpendicular to the bottom surface 11a of the grooves 11. In this case, the test object receptacle 3 can be manufactured in an easy manner.

Further, in the above-described working examples, the liquid reservoir 9 was formed in the central portion of the test object receptacle 3, this portion may be passed through to obtain a mounting portion for the chuck 15 and a supply portion such as the liquid reservoir 9 may be formed around it. Further, all the grooves 11 may be separated and liquid reservoirs 9 may be provided in respective locations.

Further, in the above-described working examples, the mold for the manufacture of the test object receptacle 3 may be formed not only by lithography, but also by etching with a reagent or plasma or machining such as cutting with a tool. The lithography may use UV rays and other radiation.

In the above-described working examples, the protrusion 9a and concave portion 9b were formed in the liquid reservoir 9 serving as a supply portion, a protrusion was present in the center of the test object receptacle 3, and a locally raised portion was formed. Therefore, the test object supplied to the liquid reservoir 9 is shifted from the portion serving as the rotation center of the test object receptacle 3, a centrifugal force created by the rotation of the test object receptacle 3 acts upon the test object, and the test object can be reliably moved even in the case of a deep liquid reservoir. However, only the protrusion 9a may be used, provided that the test object shifts from the portion serving as the rotation center of the test object receptacle 3.

Further, the convex portion 9b between the region where the protruding portions 13 are provided and the region where the protrusion 9a is provided is formed with a continuous gradual slope and a continuous slope is provided between the regions where the protrusion 9a and protruding portions 13 are provided. Therefore, when the test object supplied into the liquid reservoir 9 is moved by the centrifugal force, the test object can be moved more smoothly than in the case where a step is formed between the regions where the protrusion 9a and the protruding portions 13 are provided. However, a discontinuous portion such as a step may be also formed between the regions where the protrusion 9a and the protruding portions 13 are provided, if the test object supplied into the liquid reservoir 9 is moved by the centrifugal force.

Further, with the configuration of the above-described embodiment, as shown in FIG. 18A, the opening of the end portion of the groove 11 was provided on the outer peripheral side surface of the test object receptacle 3. However, the opening 500 of the end portion of the groove 11 may be also provided on the upper surface or lower surface of the test object receptacle 3, as shown by a wavy line in FIG. 6A. In the configuration in which the opening 500 is thus provided on the upper surface or lower surface of the test object receptacle 3, the groove 11 may be bent at a right angle, as shown in FIG. 18B and FIG. 18C, and formed so as to reach the opening on at least one of the upper side and lower side. As shown in FIG. 18D, the groove 11 may be also sequentially extended upward or downward (while being bent gently) to reach the opening 500.

With the configurations of the above-described working examples, the test object or reagent is discharged to the outside of the test object receptacle 3, but a liquid reservoir may be provided in the end portion (on the outer peripheral side) of the grooves 11 and the test object or reagent may be collected therein to prevent it from scattering. In such a configuration, too, an air drain opening is similarly provided in the liquid reservoir on the outer peripheral side of the grooves 11. Thus, it is not necessary to discharge the test object or reagent to the outside of the test object receptacle 3.

The entire disclosure of the specification, claims, summary and drawings of Japanese Patent Application No. 2004-066206 filed on Mar. 9, 2004 is hereby incorporated by reference.

What is claimed is:

1. A test object receptacle comprising:
    a disk-like main body, which is structured to be attached to an external rotary member;
    a plurality of grooves disposed radially around a central portion in the main body; and
    a plurality of adsorbent protruding portions provided inside the grooves, each adsorbent protrusion portion having a surface area positioned to contact a test object and structured to adsorb the test object, wherein:
    in at least some of the grooves, the surface area of the adsorbent protruding portions contained in a unit length of the grooves increases gradually toward a downstream side of the body with respect to a movement direction of the test object;
    during operation, the grooves are structured so that the test object moves from an upstream side of the body to the downstream side by a centrifugal force created by the external rotary member;
    a number of the adsorbent protruding portions contained in a unit length of the grooves in at least some of the grooves increases gradually toward the downstream side with respect to the movement direction of the test object; and
    a first groove of the plurality of grooves has a different shape than a second groove of the plurality of grooves.

2. The test object receptacle according to claim 1, wherein a depth of the grooves becomes gradually deeper toward the downstream side with respect to the movement direction of the test object.

3. The test object receptacle according to claim 1, wherein at least some of the grooves have a radial portion extending in a radial direction of the external rotary member and either a circumferential portion extending in a circumferential direction of the external rotary member on a downstream side of the radial portion or a meandering portion on the downstream side of the radial portion.

4. The test object receptacle according to claim 1, wherein at least some of the adsorbent protruding portions are formed integrally with a side surface of the grooves.

5. The test object receptacle according to claim 1, further comprising:
    a cover that covers the plurality of grooves, wherein at least some of the protruding portions are formed to as to protrude downward from a bottom surface of the cover and into the plurality of grooves.

6. A test apparatus comprising:
    the test object receptacle described in claim 1; and
    a rotary member which is to be joined to the test object receptacle and rotated.

7. A method for the manufacture of a mold for the manufacture of the test object receptacle described in claim 1, wherein the protruding portions are formed by a lithography.

8. The method for the manufacture of a mold according to claim 7, wherein X rays are used in the lithography.

9. A method for the manufacture of a mold for the manufacture of the test object receptacle described in claim 1, wherein the mold is formed by machining.

10. A test object receptacle which can be attached to an external rotary member, comprising:
    a plurality of grooves for supplying the test object, the grooves each having a first end close to a center of the test object receptacle and a second end at an outer end of the test object receptacle; and
    adsorbent protruding portions provided in the grooves, each protrusion portion having a surface area positioned to contact with the test object and structured to adsorb the test object, wherein:
    the surface area of the absorbent protruding portions contained in a unit length of the grooves increases gradually toward a downstream side of the test object receptacle with respect to a movement direction of the test object;
    during operation, the grooves are structured so that the test object moves from the first end of the grooves to the second end of the grooves by a centrifugal force created by the external rotary member;
    a number of the adsorbent protruding portions contained in a unit length of the grooves in at least some of the grooves increases gradually toward the downstream side with respect to the movement direction of the test object; and
    a first groove of the plurality of grooves has a different shape than a second groove of the plurality of grooves.

11. The test object receptacle according to claim 10, wherein the grooves are curved grooves.

12. The test object receptacle according to claim 10, wherein a width of a certain portion of at least one groove is wider than a width of other portions.

13. The test object receptacle according to claim 12, wherein changes in the width of the at least one groove are continuous.

14. The test object receptacle according to claim 10, wherein a width of at least one groove increases gradually toward the downstream side with respect to the movement direction of the test object.

15. The test object receptacle according to claim 10, wherein at least some of the adsorbent protruding portions are formed integrally with a side surface of the grooves.

16. The test object receptacle according to claim 10, wherein the grooves are branched.

17. The test object receptacle according to claim 16, wherein a branching point at which the grooves are branched is on a rotation center side of the external rotary member.

18. The test object receptacle according to claim 10, wherein each of the plurality of the grooves have a radially extending portion.

19. The test object receptacle according to claim 18, wherein a rotation center for a rotation provided by the external rotary member is in a center of the plurality of grooves.

20. The test object receptacle according to claim 10, wherein at least some of the grooves have a radial portion extending in a radial direction of the external rotary member and either a circumferential portion extending in a circumferential direction of the external rotary member on a downstream side of the radial portion or a meandering portion on the downstream side of the radial portion.

21. The test object receptacle according to claim 20, wherein at least some of the grooves have a second radial portion extending in a rotation direction of the external rotary member on a downstream side of either the circumferential portion or the meandering portion, in addition to the radial portion and either the circumferential portion or the meandering portion.

22. The test object receptacle according to claim 10, wherein in at least some of the grooves, the adsorbent protruding portions protrude perpendicularly to a surface where the grooves are formed.

23. The test object receptacle according to claim 10, wherein a depth of the grooves is constant.

24. The test object receptacle according to claim 10, wherein a depth of the grooves becomes gradually deeper toward the downstream side with respect to the movement direction of the test object.

25. The test object according to claim 24, wherein changes in the depth of the grooves are continuous.

26. The test object receptacle according to claim 10, wherein in the grooves, a height of the adsorbent protruding portions is directly proportional to a depth of the grooves in a location of the protruding portions.

27. The test object receptacle according to claim 10, wherein in the grooves, a shape of the adsorbent protruding portions formed in the grooves is constant.

28. The test object receptacle according to claim 10, wherein the test object receptacle is formed to have a disk-like shape.

29. The test object receptacle according to claim 10, wherein in the grooves, a spacing between the adsorbent protruding portions is within a range of 2 to 8 μm.

30. The test object receptacle according to claim 10, wherein in the grooves, a spacing between the adsorbent protruding portions is within a range of 0.3 to 2 μm.

31. The test object receptacle according to claim 10, wherein in the grooves, the adsorbent protruding portions provided in the grooves have a cylindrical shape.

32. The test object receptacle according to claim 10, wherein in the grooves, the adsorbent protruding portions are formed integrally with the grooves.

33. The test object receptacle according to claim 10, further comprising a reference portion for recognizing the test object receptacle and/or recognizing a phase in rotation of the test object receptacle.

34. The test object receptacle according to claim 33, wherein the reference portion is formed integrally with the test object receptacle.

35. The test object receptacle according to claim 10, further comprising a supply portion for supplying the test object to the grooves, wherein the supply portion has a protrusion in the center of the test object receptacle.

36. The test object receptacle according to claim 35, wherein an area surrounding the protrusion of the supply portion is concaved with respect to a region where the protruding portions are provided.

37. The test object receptacle according to claim 36, wherein an area surrounding the protrusion of the supply portion is continuously sloped.

38. The test object receptacle according to claim 10, further comprising:
a cover that covers the plurality of grooves, wherein at least some of the protruding portions are formed to as to protrude downward from a bottom surface of the cover and into the plurality of grooves.

39. A test method of intermolecular interaction using the test object receptacle described in claim 10, comprising:
supplying a test object to the grooves from a first end of the grooves which is close to a center portion of the test object receptacle;
rotating the rotary member and moving the test object by a centrifugal force along the grooves toward a second end of the grooves; and
detecting a quantity of the test object adsorbed by each adsorbent protrusion portion at a plurality of positions; and
assaying the test object based on the quantity of the test object adsorbed by each adsorbent protrusion portion at the plurality of positions.

40. The test method according to claim 39, wherein a distribution of the detected quantity of the test object with respect to a position in the grooves is computed, and the test object is assayed by using the distribution.

41. The test method according to claim 40, wherein the test object is assayed based on an area defined by restriction lines showing distribution and prescribed reference lines.

42. The test method according to claim 41, wherein the reference lines are a reference line relating to a distance in a radial direction of a rotary shaft of the rotary member and a reference line relating to the detected quantity.

43. The test method according to claim 42, wherein in some of the restriction lines, when the detected quantity is saturated, a corrected restriction line without the saturation is computed by extrapolation and the area is delineated by using the corrected restriction line.

44. A test object-receptacle, comprising:
a disk-like main body, which is structured to be attached to an external rotary member;
a plurality of grooves disposed radially around a central portion in the main body; and
a plurality of adsorbent protruding portions provided inside the grooves, each absorbent protrusion portion having a surface area positioned to contact the test object and structured to adsorb the test object, wherein:
at least one groove is branched into two grooves toward an outer periphery of the main body; and
a liquid reservoir is linked to each of the branched two grooves on a side close to a center thereof.

* * * * *